United States Patent [19]
Estes et al.

[11] Patent Number: 5,551,418
[45] Date of Patent: Sep. 3, 1996

[54] SLEEP APNEA TREATMENT APPARATUS WITH RESET CIRCUITRY

[75] Inventors: Mark C. Estes, Irwin; Janice M. Cattano, Gibsonia, both of Pa.

[73] Assignee: Respironics, Inc., Murrysville, Pa.

[21] Appl. No.: 110,372

[22] Filed: Aug. 23, 1993

Related U.S. Application Data

[63] Continuation-in-part of Ser. No. 768,269, Oct. 17, 1991, Pat. No. 5,239,995.

[51] Int. Cl.[6] .......................... A61M 16/00; A62B 7/00; F16K 31/02
[52] U.S. Cl. .................. 128/204.23; 128/204.21
[58] Field of Search .......... 128/204.18, 204.21–204.23, 128/204.26

[56] References Cited

U.S. PATENT DOCUMENTS

| | | | |
|---|---|---|---|
| 4,003,377 | 1/1977 | Dahl | 128/204.23 |
| 4,393,869 | 7/1983 | Boyarsky et al. | 128/204.18 |
| 4,550,726 | 11/1985 | McEwen | 128/204.23 |
| 5,107,830 | 4/1992 | Younes | 128/204.18 |
| 5,117,819 | 6/1992 | Servidio et al. | 128/204.23 |
| 5,134,995 | 8/1992 | Gruenke et al. | 128/204.23 |
| 5,148,802 | 9/1992 | Sanders et al. | 128/204.26 |
| 5,165,397 | 11/1992 | Arp | 128/204.23 |
| 5,199,424 | 4/1993 | Sullivan et al. | 128/204.18 |
| 5,203,343 | 4/1993 | Axe et al. | 128/725 |
| 5,239,995 | 8/1993 | Estes et al. | 128/204.23 |
| 5,313,937 | 5/1994 | Zdrojkowski | 128/204.23 |

*Primary Examiner*—Kimberly L. Asher
*Attorney, Agent, or Firm*—Reed Smith Shaw & McClay

[57] ABSTRACT

Improved methodology and apparatus for the clinical study and treatment of sleep apnea which incorporates one or more of the following features: (1) application of mono-level, alternating high and low level, or variable positive airway pressure generally within the airway of the patient with the mono-level, high and low level, or variable airway pressure generally being coordinated with and/or responsive to the spontaneous respiration of the patient, (2) usage of adjustably programmable pressure ramp circuitry capable of producing multiple pressure ramp cycles of predetermined duration and pattern whereby the ramp cycles may be customized to accommodate the specific needs of an individual sleep apnea patient so as to ease the patient's transition from wakefulness to sleep, (3) remote control or patient-sensed operation of the apparatus, (4) employment of safety circuitry, reset circuitry and minimum system leak assurance circuitry, controls and methods, and (5) utilization of clinical control circuitry whereby sleep disorder data may be compiled and appropriate therapy implemented during a one-night sleep study.

7 Claims, 17 Drawing Sheets

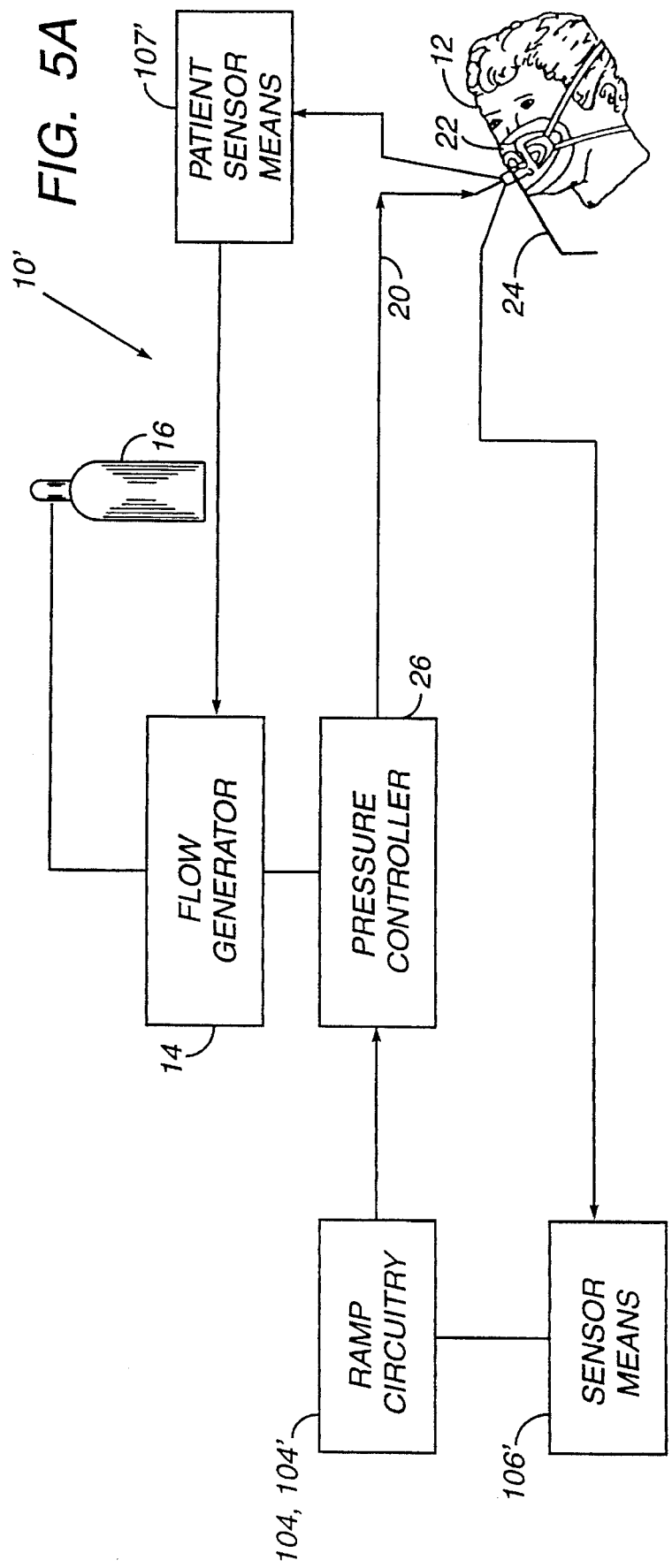

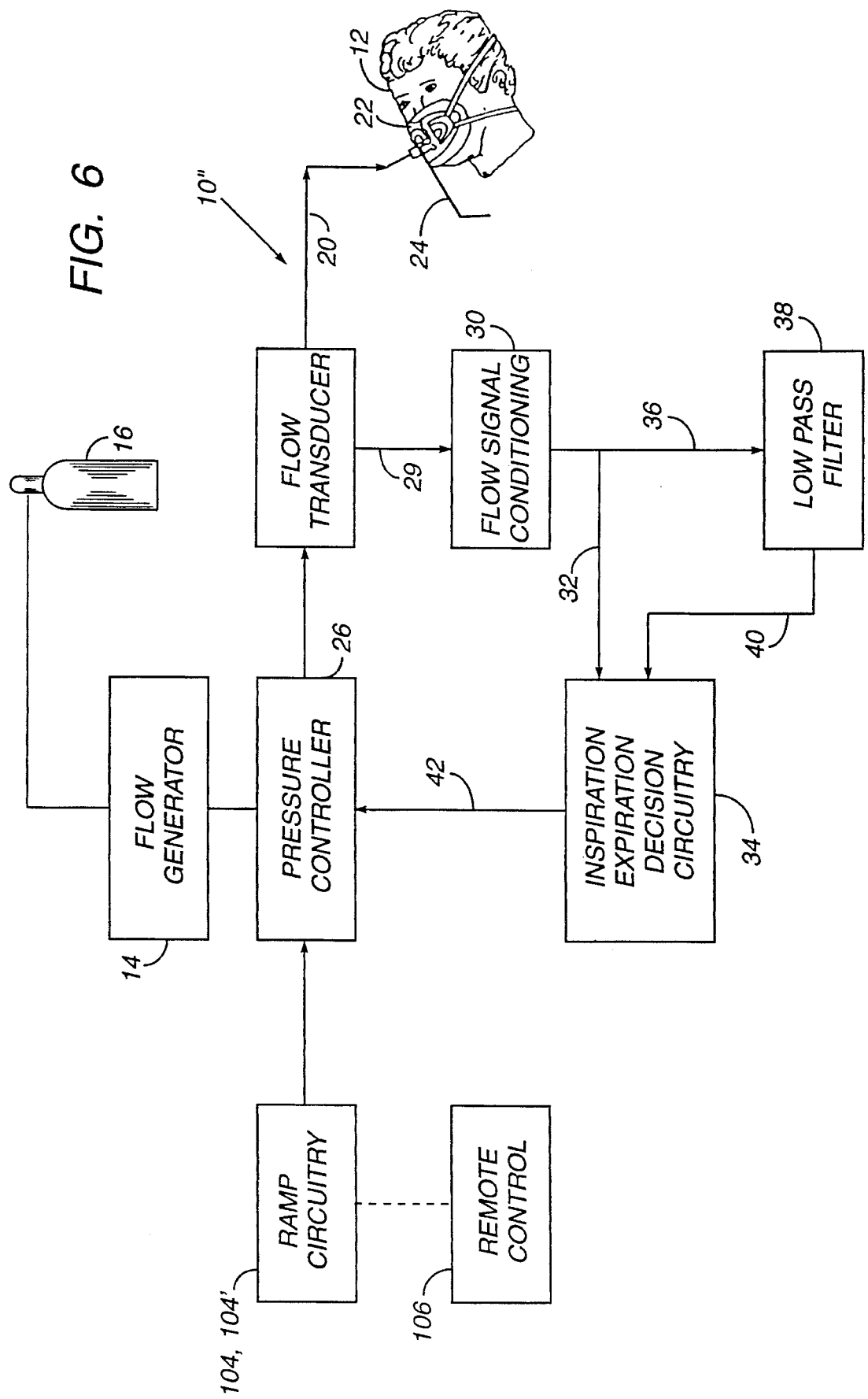

SLEEP APNEA TREATMENT APPARATUS WITH RESET CIRCUITRY

CROSS REFERENCE TO RELATED APPLICATIONS

This application is a continuation-in-part of U.S. patent application Ser. No. 07/768,269, filed Oct. 1, 1991, of the same title, which is now U.S. Pat. No. 5,239,995, issued Aug. 31, 1993.

FIELD OF THE INVENTION

The present invention relates generally to methodology and apparatus for treatment of sleep apnea and, more particularly, to mono-level, bi-level and variable positive airway pressure apparatus, as well as feedback type versions thereof, including circuitry for enabling a patient to selectively actuate one or more pressure ramp cycles wherein, during each ramp cycle, available airway pressure increases with time from a predetermined minimum pressure value to a prescription pressure, thereby facilitating the patient's transition from a waking to a sleeping state.

BACKGROUND OF THE INVENTION

The sleep apnea syndrome afflicts an estimated 1% to 5% of the general population and is due to episodic upper airway obstruction during sleep. Those afflicted with sleep apnea experience sleep fragmentation and intermittent, complete or nearly complete cessation of ventilation during sleep with potentially severe degrees of oxyhemoglobin desaturation. These features may be translated clinically into extreme daytime sleepiness, cardiac arrhythmias, pulmonary-artery hypertension, congestire heart failure and/or cognitive dysfunction. Other sequelae of sleep apnea include right ventricular dysfunction with cor pulmonale, carbon dioxide retention during wakefulness as well as during sleep, and continuous reduced arterial oxygen tension. Hypersomnolent sleep apnea patients may be at risk for excessive mortality from these factors as well as by an elevated risk for accidents while driving and/or operating potentially dangerous equipment.

Although details of the pathogenesis of upper airway obstruction in sleep apnea patients have not been fully defined, it is generally accepted that the mechanism includes either anatomic or functional abnormalities of the upper airway which result in increased air flow resistance. Such abnormalities may include narrowing of the upper airway due to suction forces evolved during inspiration, the effect of gravity pulling the tongue back to appose the pharyngeal wall, and/or insufficient muscle tone in the upper airway dilator muscles. It has also been hypothesized that a mechanism responsible for the known association between obesity and sleep apnea is excessive soft tissue in the anterior and lateral neck which applies sufficient pressure on internal structures to narrow the airway.

The treatment of sleep apnea has included such surgical interventions as uvulopalatopharyngoplasty, gastric surgery for obesity, and maxillo-facial reconstruction. Another mode of surgical intervention used in the treatment of sleep apnea is tracheostomy. These treatments constitute major undertakings with considerable risk of postoperative morbidity if not mortality. Pharmacologic therapy has in general been disappointing, especially in patients with more than mild sleep apnea. In addition, side effects from the pharmacologic agents that have been used are frequent. Thus, medical practitioners continue to seek non-invasive modes of treatment for sleep apnea with high success rates and high patient compliance including, for example in cases relating to obesity, weight loss through a regimen of exercise and regulated diet.

Recent work in the treatment of sleep apnea has included the use of continuous positive airway pressure (CPAP) to maintain the airway of the patient in a continuously open state during sleep. For example, U.S. Pat. No. 4,655,213 and Australian Pat. No. AU-B-83901/82 both disclose sleep apnea treatments based on continuous positive airway pressure applied within the airway of the patient.

Also of interest is U.S. Pat. No. 4,773,411 which discloses a method and apparatus for ventilatory treatment characterized as airway pressure release ventilation and which provides a substantially constant elevated airway pressure with periodic short term reductions of the elevated airway pressure to a pressure magnitude no less than ambient atmospheric pressure.

U.S. Pat. No. 5,199,424 and published PCT Application No. WO 88/10108 describes a CPAP apparatus which includes a feedback system for controlling the output pressure of a variable pressure air source whereby output pressure from the air source is increased in response to detection of sound indicative of snoring. According to additional embodiments of the apparatus disclosed in these references, a pressure ramp cycle (i.e., a gradual increase in output pressure) may occur upon initial activation of the apparatus which gradually increases output pressure from a predetermined minimum to a predetermined maximum or therapeutic pressure specifically selected for the patient.

Publications pertaining to the application of CPAP in treatment of sleep apnea include the following:
1. Lindsay, DA, Issa FG, and Sullivan C. E. "Mechanisms of Sleep Desaturation in Chronic Airflow Limitation Studied with Nasal Continuous Positive Airway Pressure (CPAP), "*Am Rev Respir Dis,* 1982; 125: p. 112.
2. Sanders NH, Moore SE, Eveslage J. "CPAP via nasal mask: A treatment for occlusive sleep apnea, *Chest,* 1983; 83: pp. 144–145.
3. Sullivan CE, Berthon-Jones M. Issa FG. "Remission severe obesity-hypoventilation syndrome after short-term treatment during sleep with continuous positive airway pressure, *Am Rev Respir Dis,* 1983; 128: pp. 177–181.
4. Sullivan CE, Issa FG, Berthon-Jones M., Eveslage J. "Reversal of obstructive sleep apnea by continuous positive airway pressure applied through the nares, *Lancet,* 1981; 1: pp. 862–865.
Sullivan CE, Berthon-Jones M. Issa FG. "Treatment of obstructive apnea with continuous positive airway pressure applied through the nose. *Am Rev Respir Dis,* 1982; 125: p. 107. Annual Meeting Abstracts.
6. Rapoport DM, Sorkin B, Garay SM, Goldring RN. "Reversal of the 'Pickwickian Syndrome' by long-term use of nocturnal nasal-airway pressure," *N Engl J. Med,* 1982; 307: pp. 931–933.
7. Sanders MH, Holzer BC, Pennock BE. "The effect of nasal CPAP on various sleep apnea patterns, *Chest,* 1983; 84: p. 336. Presented at the Annual Meeting of the American College of Chest Physicians, Chicago ILL., October 1983.
8. Sanders, MH. "Nasal CPAP Effect on Patterns of Sleep Apnea", Chest 1984; 86:83914 844

Although mono-level positive airway pressure or CPAP has been found to be very effective and well accepted, it suffers from some of the same limitations, although to a lesser degree, as do the surgery options; specifically a significant proportion of sleep apnea patients do not tolerate CPAP well. Thus, development of other viable non-invasive therapies has been a continuing objective in the art.

SUMMARY OF THE INVENTION

The present invention contemplates a novel and improved method for treatment of sleep apnea as well as novel methodology and apparatus for carrying out such improved treatment method. The invention contemplates the treatment of sleep apnea through application of pressure at variance with ambient atmospheric pressure within the upper airway of the patient in a manner to promote patency of the airway to thereby relieve upper airway occlusion during sleep.

In a first embodiment of the invention, positive pressure is applied at a substantially constant, patient-specific prescription pressure within the airway of the patient to maintain the requisite patent or "splint" force to sustain respiration during sleep periods. This form of treatment is commonly known as mono-level CPAP therapy.

In another embodiment of the invention, pressure is applied alternately at relatively higher and lower prescription pressure levels within the airway of the patient so that the pressure-induced patent force applied to the patients airway is alternately a larger and a smaller magnitude force. The higher and lower magnitude positive prescription pressure levels, which will be hereinafter referred to by the acronyms IPAP (inspiratory positive airway pressure) and EPAP (expiratory positive airway pressure), may be initiated by spontaneous patient respiration, apparatus preprogramming, or both, with the higher magnitude pressure (IPAP) being applied during inspiration and the lower magnitude pressure (EPAP) being applied during expiration. This method of treatment may descriptively be referred to as bi-level therapy. In bi-level therapy, it is EPAP which has the greater impact upon patient comfort. Hence, the treating physician must be cognizant of maintaining EPAP as low as is reasonably possible to maintain sufficient pharyngeal patency during expiration, while optimizing user tolerance and efficiency of the therapy.

This latter embodiment contemplates a novel and improved apparatus which is operable in accordance with a novel and improved method to provide sleep apnea treatment. More specifically, a flow generator and an adjustable pressure controller supply air flow at a predetermined, adjustable pressure to the airway of a patient through a flow transducer. The flow transducer generates an output signal which is then conditioned to provide a signal proportional to the instantaneous flow rate of air to the patient. The instantaneous flow rate signal is fed to a low pass filter which passes only a signal indicative of the average flow rate over time. The average flow rate signal typically would be expected to be a value representing a positive flow as the system is likely to have at least minimal leakage from the patient circuit (e.g., small leaks about the perimeter of the respiration mask worn by the patient). The average flow signal is indicative of such leakage because the summation of all other components of flow over time must be essentially zero since inspiration flow must equal expiration flow volume over time, that is, over a period of time the volume of air breathed in equals the volume of the gases breathed out.

Both the instantaneous flow signal and the average flow rate signal are fed to an inspiration/ expiration decision module which is, in its simplest form, a comparator that continually compares the input signals and provides a corresponding drive signal to the pressure controller. In general, when the instantaneous flow exceeds average flow, the patient is inhaling and the drive signal supplied to the pressure controller sets the pressure controller to deliver air, at a preselected elevated pressure, to the airway of the patient. Similarly, when the instantaneous flow rate is less than the average flow rate, the patient is exhaling and the decision circuitry thus provides a drive signal to set the pressure controller to provide a relatively lower magnitude of pressure in the airway of the patient. The patient's airway thus is maintained open by alternating higher and lower magnitudes of pressure which are applied during spontaneous inhalation and exhalation, respectively.

As has been noted, some sleep apnea patients do not tolerate standard, i.e., mono-level, CPAP therapy. Specifically, approximately 25% of patients cannot tolerate CPAP due to the attendant discomfort. Standard CPAP mandates equal pressures (i.e., a single prescription pressure) during both inhalation and exhalation. The elevated pressure during both phases of breathing may create difficulty in exhaling and the sensation of an inflated chest. However, we have determined that although both inspiratory and expiratory air flow resistances in the airway are elevated during sleep preceding the onset of apnea, the airway flow resistance may be less during expiration than during inspiration. Thus it follows that the bi-level therapy of our invention as characterized above may be sufficient to maintain pharyngeal patency during expiration even though the pressure applied during expiration is not as high as that needed to maintain pharyngeal patency during inspiration. In addition, some patients may have increased upper airway resistance primarily during inspiration with resulting adverse physiologic consequences. Thus, our invention also contemplates applying elevated pressure only during inhalation thus eliminating the need for global (inhalation and exhalation) increases in airway pressure. The relatively lower pressure applied during expiration may in some cases approach or equal ambient pressure. The lower pressure applied in the airway during expiration enhances patient tolerance by alleviating some of the uncomfortable sensations normally associated with CPAP.

Under prior CPAP therapy, pressures as high as 20 cm $H_2O$ have been required, and some patients on nasal CPAP thus have been needlessly exposed to unnecessarily high expiratory pressures with the attendant discomfort and elevated mean airway pressure, and theoretic risk of barotrauma. Our invention permits independent application of a higher inspiratory airway pressure in conjunction with a lower expiratory airway pressure in order to provide a therapy which is better tolerated by the 25% of the patient population which does not tolerate CPAP therapy, and which may be safer and more comfortable in the other 75% of the patient population.

As has been noted hereinabove, the switch between higher and lower prescription pressure magnitudes can be controlled by spontaneous patient respiration, apparatus preprogramming, or both. Hence, the manufacturer or the clinician can govern respiration rate and volume or, alternatively, this capability may be independently ascribed to the patient. As has been also noted, the invention contemplates automatic compensation for system leakage whereby nasal mask fit and air flow system integrity are of less consequence than in the prior art. In addition to the benefit of automatic leak compensation, other important benefits of the invention include lower mean airway pressures for the patient and enhanced safety, comfort and tolerance.

In all embodiments, the present invention makes use of "ramp" circuitry operatively connected to pressure control means of the apparatus and selectively activatable by the patient to effect at least one pressure "ramp cycle" which is described in greater detail below. The maximum duration(s) of the ramp cycle(s), the shape(s) of the ramp curve(s) and the prescription pressure(s) are normally established by a sleep study of the patient and this data can be programmed into the apparatus of the instant invention. It is also desirable that the apparatus be operable either by manual controls located directly on the apparatus or via remote control.

Approximately 25% of all patients who undergo CPAP therapy for sleep apnea experience respiration discomfort and find it difficult to fall asleep because of the therapy. The purpose of a ramp cycle is to alleviate this discomfort. A ramp cycle is an automatic cycle that, once activated, causes the apparatus (mono-level, bi-level or variable) to output a predetermined minimum positive pressure at or above ambient pressure which is gradually increased over a predetermined time period known as "ramp time" during which the patient begins to fall asleep. Upon expiration of the ramp time the patient typically has fallen asleep and at such time the pressure produced by the apparatus is that of the patient's therapy prescription pressure(s) whereupon the patient receives normal treatment as he sleeps.

A particular advantage of the present invention is that the unique ramp circuitry enables not only an initial ramp cycle to be achieved for when one first attempts to sleep but such circuitry also permits one or more additional cycles to be selectively activated by the user at instances where the user awakens during an extended rest period, or when the user fails to fall asleep during the first ramp cycle and again requires a ramp cycle to fall back to sleep, or even within (i.e., during) an already ongoing ramp cycle. Typically, during a sleeping period of several hours, the time required to once again fall asleep after briefly being awakened is generally less than the time spent initially falling asleep. To accommodate this phenomenon, the ramp circuitry of the instant invention allows adjustment of the ramp time of any additional ramp cycle to run for a selected fraction of the initial ramp time, which itself may be a pre-programmed, patient-selected a clinician-selected fraction of a prescription time preset by a health care professional in supervision of the patient's sleep apnea treatment.

The ramp circuitry enables a physician or other health care worker to set the initial ramp time(s) and prescription pressure(s). Additionally, however, the novel ramp circuitry of the present invention permits adjustment of the "shape" of the pressure ramp curve, whereby the physician, health care worker or patient can suitably manipulate appropriate controls associated with the ramp circuitry to control the pressure output pattern of the ramp (as represented as a function of pressure versus time) such that it may assume virtually any configuration including, inter alia, linear, stepped, or curvilinear slope, depending upon a patient's particular needs as dictated by the results of the patient's sleep study. In the case of bi-level systems according to the instant invention, the ramp circuitry also affords, for example, simultaneous, independent, identical or differential ramping of IPAP and EPAP. Alternatively, the parameters establishable by the ramp circuitry may also be preprogrammed by the manufacturer.

Additionally, sufferers of sleep apnea are sometimes afflicted by other maladies which limit the degree to which they may safely physically exert themselves. An advantage of the present invention is that it enables a limited-mobility user, at his discretion, to operate the apparatus either by manual controls located directly on the apparatus or via remote control. Equally as important, it provides any sleep apnea sufferer using the apparatus with the peace of mind of knowing that the pressure can be reduced at any time via the remote control. Further, the preferred embodiment of the remote control contemplated for use in the present invention is one which the user can operate easily and reliably either in light or darkness to turn the apparatus on and off as well as selectively activate the first or subsequent ramp cycles.

As additional or alternative design features, the apparatus may include an automatic ON/OFF mechanism and/or alternative ramp activation means.

The automatic ON/OFF mechanism desirably comprises a sensor means situated within or proximate to the patient's breathing circuit. Such breathing circuit will be understood to include, but is not limited to, the gas flow conduit, the gas flow generator means and the respiratory interface, e.g., oral mask, nasal mask, oral/ nasal mask, endotracheal tube, nasal cannulae, or other suitable appliance. The sensor means may assume the form of a pressure, flow, thermal, audio, optic, electrical current, voltage, force, displacement or other suitable transducer which detects the presence (and/absence) of the patient. More particularly, according to a first mode of operation, when the respiratory interface is appropriately positioned over the patient's face, the sensor means will operate so as to detect at least one of the above-mentioned conditions indicative of the patient's presence and generate a signal that is transmitted to the flow generator to activate the apparatus. In a second mode of operation, the sensor means may be designed solely for apparatus activation purposes. Hence, upon removal of the respiratory interface, the sensor means would fail to detect any conditions indicative of the patient's presence and, therefore, generate an appropriate signal to deactivate the apparatus. A third mode of operation combines these functions. That is, the sensor means may be operable to detect both the presence and absence of the patient and generate a signal to activate the apparatus upon detection of a condition indicative of the patient's presence, as well as an apparatus deactivation signal upon failure of detecting such a condition, i.e., the patient's absence.

The alternative ramp activation means may comprise a sensor means responsive to signals of selected magnitude and/or frequency consciously produced by the patient. In accordance with a presently preferred embodiment, the alternative ramp activations means may comprise a pressure transducer, for instance, a microphone located within or near the patient's respiratory interface, associated gas flow conduit or gas flow generator and capable of detecting sound of a limited frequency range spanning that associated with human speech. So configured, the transducer would be nonresponsive to common ambient sounds produced by the user (e.g., coughing or sneezing), machinery noise, music or animal sounds. Moreover, by being isolated through its enclosure within the gas flow system, the transducer would detect only the patient's speech to the exclusion of others in the vicinity or speech emanating from television or radio sources. Upon detection of the patient's speech such as, for example, when the patient awakens and speaks to start a new ramp cycle, the audio transducer generates and transmits an activation signal to the ramp circuitry to initiate the desired ramp cycle. The sensor may alternatively be operable to begin a ramp cycle in response to detection of a predetermined pattern of inhalations and/or exhalations or other conscious actions by the patient.

As noted hereinabove, the ramp circuitry, remote or automatic ON/OFF mechanisms and/or remote or pressure responsive ramp activation means may be incorporated and utilized with success in mono-level, bi-level and variable positive airway pressure ventilation apparatus or patient-responsive feedback type versions thereof, an example of one version of which will be described in greater detail hereinafter. Other embodiments of the invention employ novel system control circuitry including reset circuitry, safety circuitry, therapy delay circuitry and/or minimum system leakage assurance circuitry which may also be used in conjunction with mono-level, bi-level and variable level ventilation apparatus, but find especially beneficial application with feedback type versions of those ventilation apparatus because of their particular manner of operation.

Briefly, the system reset circuitry permits the patient (if suddenly awakened, for example) to instantaneously reset the system output pressure to a predetermined reduced pressure after which the treatment may then proceed as it did prior to reset. An advantage attendant to both the ramp circuitry and reset circuitry is that they both afford the patient the opportunity to immediately respire against a reduced pressure once awakened, thereby enhancing patient comfort and transition back to a sleeping state. Unlike the ramp circuitry, however, the reset circuitry permits the patient to more rapidly receive the full benefits of the positive airway pressure therapy since therapy resumes instantaneously upon reset. Such modality, as will be appreciated, is more likely to be exercised by a patient who generally experiences little difficulty in falling back to sleep after being awakened during an extended period of sleep.

The safety circuitry of the present invention allows the patient or his overseeing health care professional to establish minimum and maximum system output pressures below and above which the system will not dispense pressurized gas. The minimum pressure will, of course, be at least zero and, preferably, a threshold pressure sufficient to maintain pharyngeal patency during expiration. The maximum pressure, on the other hand, will be some pressure somewhat less than that which would result in over-inflation and perhaps rupture of the patient's lungs. The safety circuitry functions differently than the prescription pressure controls of the ramp circuitry. That is, instead of establishing lower and upper prescription pressures to be applied during normal usage of the apparatus it sets absolute minimum and maximum fail-safe output pressure limits which will not be exceeded, and therefore potentially cause physical harm to the patient, in the event other system components malfunction.

The therapy delay circuitry proposed herein permits a patient to be diagnosed and treated during a single sleep study. Typically, the practice has been for the patient to undergo two sleep studies at an appropriate observation facility such as a hospital, clinic or laboratory. The first night is spent observing the patient in sleep and recording selected parameters such as oxygen saturation, chest wall abdominal movement, air flow, expired $CO_2$, ECG, EEG, EMG and eye movement. This information can be interpreted to diagnose the nature of the sleeping disorder and confirm the presence or absence of apnea and, where present, the frequency of apneic episodes and extent and duration of associated oxygen desaturation. Apneas can be identified as obstructive, central or mixed.

The second night is spent with the patient undergoing nasal positive airway pressure therapy. When apnea is observed the pressure setting is increased as required to determine the maximum pressure necessary to prevent apnea. As for determining the minimum pressure required to prevent occlusions, for a given patient in a given physical condition there normally will be found different minimum pressures for various stages of sleep. Thus, the appropriate minimum pressure discovered in the laboratory is necessarily the maximum of all minimum pressures recorded for that particular night and may not necessarily be the ideal minimum pressure for all occasions.

The therapy delay circuitry of the instant invention is operable to suppress the therapy for any desired period of time while associated data storage and retrieval means compile data associated with selected ones of the patient's physiological parameters to be used for diagnosis of the patient's particular sleep disorder. Once sufficient data is recorded, system control adjustments based upon the data may be inputted as appropriate and the therapy delay circuitry may be switched from its therapy suppression mode to a therapy application mode, whereby treatment specifically adapted and responsive to the patient's observed physiological condition may be effectively implemented in a single night in the sleep study facility. With the costs of daily hospital and related medical stays ever on the rise, the advantage of reducing the length of the patient's sleep study to potentially half of what otherwise would be required is self-evident.

The present invention also provides for minimum system leakage assurance circuitry, the function of which is to assure that the system discharges a minimum leakage flow during therapy, i.e., when the patient is asleep or attempting to fall asleep. The minimum system leakage assurance circuitry desirably comprises an adjustable leakage test pressure control, an adjustable pre-therapy pressure control, an adjustable timer, and a switch. The switch is responsive to the timer and triggers the leakage test pressure control to transmit a signal causing the apparatus to output a preset leakage test pressure. The switch is also operable to trigger the pre-therapy pressure control to transmit a signal causing the apparatus to output a preset pre-therapy pressure. The preset leakage test pressure may be the peak pressure output by the apparatus during the previous night or some other desired pressure, whereas the pre-therapy pressure may be the minimum pressure output by the apparatus during the previous night or some other pressure.

Using the timer, after the apparatus is activated the system will output the leakage test pressure to temporarily overpressurize the gas flow circuit for some preselected period of time. This time period will normally be sufficient for the patient to properly position and seal the mask on his face and adjust any gas conduit connections such that system leakage flow is brought to a minimum. After the passage of the prescribed time period, the timer triggers the switch to activate the pre-therapy pressure control, thereby causing the system to output the selected pre-therapy pressure for a specified duration also established by the timer. After expiration of the designated time for pre-therapy pressure application, the timer then urges the switch to assume a neutral position whereby the apparatus outputs its mono-level, bi-level or variable ventilation pressure therapy.

An advantage of such an arrangement is that by temporarily overpressurizing the gas flow circuit prior to treatment, unwanted system leaks can be discovered and sealed before the patient falls asleep. Hence, leakage flow (or average system flow) and its associated pressure can be minimized while the patient sleeps, thereby enhancing patient comfort. In lieu of or addition to the timer, the minimum system leakage assurance circuitry may also include a low leak detector. The low leak detector detects whether the system, under the application the leak test pressure, outputs a leakage flow less than a predetermined minimum. If a sufficiently low leakage flow is detected, the low leak detector automatically overrides the timer and triggers the pre-therapy pressure control to cause the system to output the specified pre-therapy pressure for the preset time and then output the appropriate therapy pressure.

Similarly, in addition to or in lieu of the timer and/or the low leak detector, the minimum system leakage assurance circuitry may include a manual override, e.g., an audio transducer, which responds to patient initiated commands to override the timer in a manner similar to the low leak detector.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein:

FIG. 5A is a functional block diagram of a further embodiment of an apparatus according to the instant invention;

FIG. 6 is a functional block diagram of a further embodiment of an apparatus according to the instant invention;

DETAILED DESCRIPTION OF THE INVENTION

Figure 1:
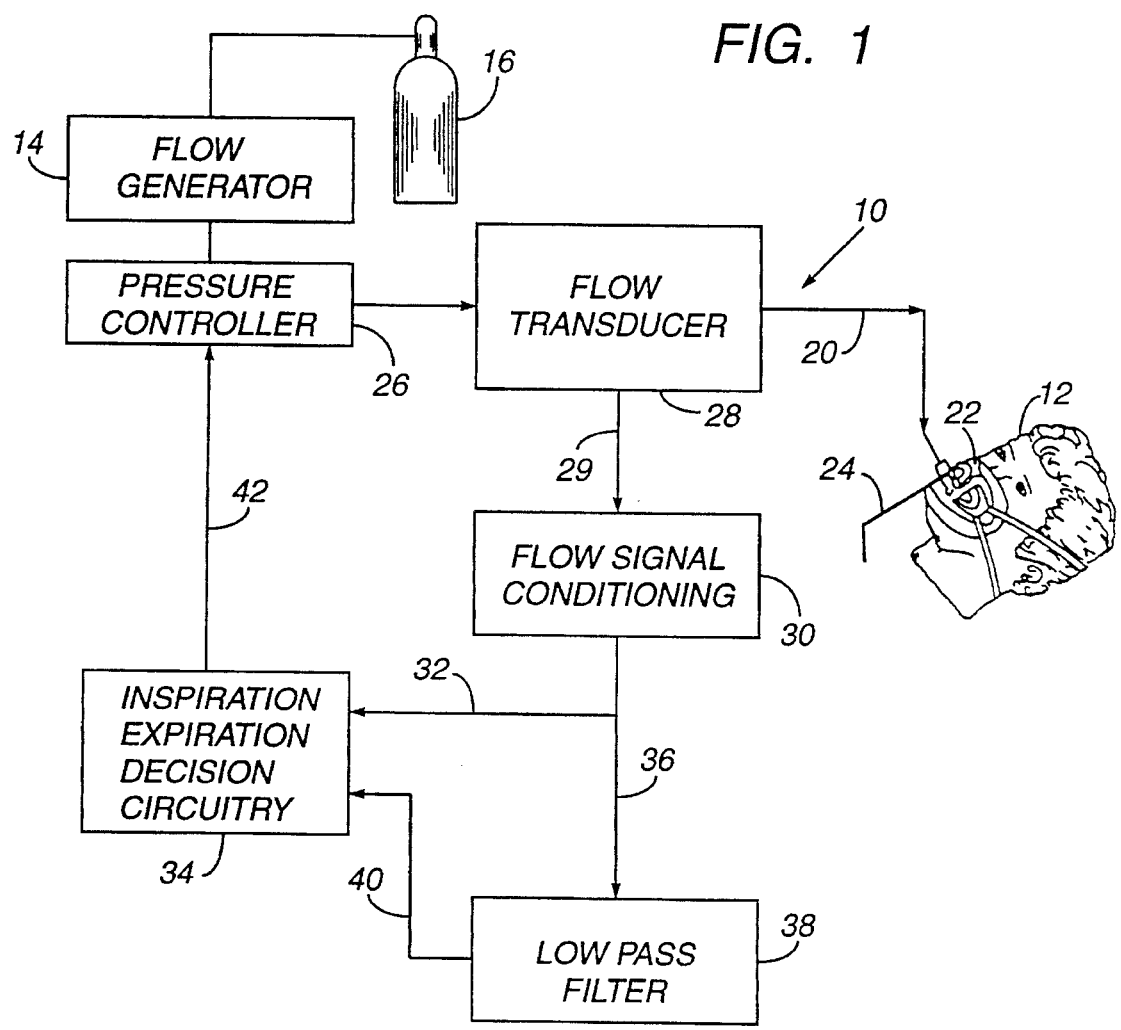
FIG. 1 is a functional block diagram of an apparatus according to the instant invention.

There is generally indicated at 10 in FIG. 1 an apparatus according to one presently preferred embodiment of the instant invention and shown in the form of a functional block diagram. Apparatus 10 is operable according to a novel process which is another aspect of the instant invention for delivering breathing gas such as air alternately at relatively higher and lower pressures (i.e., equal to or above ambient atmospheric pressure) to a patient 12 for treatment of the condition known as sleep apnea.

Apparatus 10 comprises a gas flow generator 14 (e.g., a blower) which receives breathing gas from any suitable source, a pressurized bottle 16 or the ambient atmosphere, for example. The gas flow from flow generator 14 is passed via a delivery conduit 20 to a breathing appliance such as a mask 22 of any suitable known construction which is worn by patient 12. The mask 22 may preferably be a nasal mask or a full face mask as shown. Other breathing appliances which may be used in lieu of a mask include nasal cannulae, an endotracheal tube, or any other suitable appliance for interfacing between a source of breathing gas and a patient.

The mask 22 includes a suitable exhaust port means, schematically indicated at 24, for exhaust of breathing gases during expiration. Exhaust port 24 preferably is a continuously open port which imposes a suitable flow resistance upon exhaust gas flow to permit a pressure controller 26, located in line with conduit 20 between flow generator 14 and mask 22, to control the pressure of air flow within conduit 20 and thus within the airway of the patient 12. For example, exhaust port 24 may be of sufficient cross-sectional flow area to sustain a continuous exhaust flow of approximately 15 liters per minute. The flow via exhaust port 24 is one component, and typically the major component of the overall system leakage, which is an important parameter of system operation. In an alternative embodiment to be discussed hereinbelow, it has been found that a non-rebreathing valve may be substituted for the continuously open port 24.

The pressure controller 26 is operative to control the pressure of breathing gas within the conduit 20 and thus within the airway of the patient. Pressure controller 26 is located preferably, although not necessarily, downstream of flow generator 14 and may take the form of an adjustable valve which provides a flow path which is open to the ambient atmosphere via a restricted opening, the valve being adjustable to maintain a constant pressure drop across the opening for all flow rates and thus a constant pressure within conduit 20.

Also interposed in line with conduit 20, preferably downstream of pressure controller 26, is a suitable flow transducer 28 which generates an output signal that is fed as indicated at 29 to a flow signal conditioning circuit 30 for derivation of a signal proportional to the instantaneous flow rate of breathing gas within conduit 20 to the patient.

It will be appreciated that flow generator 14 is not necessarily a positive displacement device. It may be, for example, a blower which creates a pressure head within conduit 20 and provides air flow only to the extent required to maintain that pressure head in the presence of patient breathing cycles, the exhaust opening 24, and action of pressure controller 26 as above described. Accordingly, when the patient is exhaling, peak exhalation flow rates from the lungs may far exceed the flow capacity of exhaust port 24. As a result, exhalation gas back flows within conduit 20 through flow transducer 28 and toward pressure controller 26, and the instantaneous flow rate signal from transducer 28 thus will vary widely within a range from relatively large positive (i.e., toward the patient) flow to relatively large negative (i.e., from the patient) flow.

The instantaneous flow rate signal from flow signal conditioning circuitry 30 is fed as indicated at 32 to a decision module 34, a known comparator circuit for example, and is additionally fed as indicated at 36 to a low pass filter 38. Low pass filter 38 has a cutoff frequency low enough to remove from the instantaneous flow rate input signal most variations in the signal which are due to normal breathing.

Low pass filter 38 also has a long enough time constant to ensure that spurious signals, aberrant flow patterns and peak instantaneous flow rate values will not dramatically affect system average flow. That is, the time constant of low pass filter 38 is selected to be long enough that it responds slowly to the instantaneous flow rate signal input. Accordingly, most instantaneous flow rate input signals which could have a large impact on system average flow in the short term have a much smaller impact over a longer term, largely because such instantaneous flow rate signal components will tend to cancel over the longer term. For example, peak instantaneous flow rate values will tend to be alternating relatively large positive and negative flow values corresponding to peak inhalation and exhalation flow achieved by the patient during normal spontaneous breathing. The output of low pass filter 38 thus is a signal which is proportional to the average flow in the system, and this is typically a positive flow which corresponds to average system leakage (including flow from exhaust 24) since, as noted, inhalation and exhalation flow cancel for all practical purposes.

The average flow signal output from the low pass filter 38 is fed as indicated at 40 to decision circuitry 34 where the instantaneous flow rate signal is continually compared to the system average flow signal. The output of the decision circuitry 34 is fed as a drive signal indicated at 42 to control the pressure controller 26. The pressure magnitude of breathing gas within conduit 20 thus is coordinated with the spontaneous breathing effort of the patient 12, as follows.

When the patient begins to inhale, the instantaneous flow rate signal goes to a positive value above the positive average flow signal value. Detection of this increase in decision circuitry 34 is sensed at the start of patient inhalation. The output signal from decision circuitry 34 is fed to pressure controller 26 which, in response, provides higher pressure gas flow within conduit 20 and thus higher pressure within the airway of the patient 12. This is the higher magnitude pressure value of our bi-level system and is referred to hereinbelow as IPAP (inhalation positive airway pressure). During inhalation, the flow rate within conduit 20 will increase to a maximum and then decrease as inhalation comes to an end.

At the start of exhalation, air flow into the patient's lungs is nil and as a result the instantaneous flow rate signal will be less than the average flow rate signal which, as noted is a relatively constant positive flow value. The decision circuitry 34 senses this condition at the start of exhalation and provides a drive signal to pressure controller 26 which, in response, provides gas flow within conduit 20 at a lower pressure which is the lower magnitude pressure value of the bi-level system, referred to hereinbelow as EPAP (exhalation positive airway pressure). As has been noted hereinabove the range of EPAP pressures may include ambient atmospheric pressure. When the patient again begins spontaneous inhalation, the instantaneous flow rate signal again increases over the average flow rate signal, and the decision circuitry once again feeds a drive signal to pressure controller 26 to reinstitute the IPAP pressure.

System operation as above specified requires at least periodic comparison of the input signals 32 and 40 by decision circuitry 34. Where this or other operations are described herein as continual, the scope of meaning to be ascribed includes both continuous (i.e., uninterrupted) or periodic (i.e., at discrete intervals).

As has been noted, the system 10 has a built-in controlled leakage via exhaust port 24 thus assuring that the average flow signal will be at least a small positive flow. During inhalation, the flow sensed by the flow transducer will be the sum of exhaust flow via port 24 and all other system leakage downstream of transducer 28, and inhalation flow within the airway of the patient 12. Accordingly, during inhalation the instantaneous flow rate signal as conditioned by conditioning module 30, will reliably and consistently reflect inhalation flow exceeding the average flow rate signal. During exhalation, the flow within conduit 20 reverses as exhalation flow from the lungs of the patient far exceeds the flow capacity of exhaust port 24. Accordingly, exhalation air backflows within conduit 20 past transducer 28 and toward pressure controller 26. Since pressure controller 26 is operable to maintain set pressure, it will act in response to flow coming from both the patient and the flow generator to open an outlet port sufficiently to accommodate the additional flow volume and thereby maintain the specified set pressure as determined by action of decision circuitry 34.

In both the inhalation and exhalation cycle phases, the pressure of the gas within conduit 20 exerts a pressure within the airway of the patient to maintain an open airway and thereby alleviate airway constriction.

In practice, it may be desirable to provide a slight offset in the switching level within decision circuitry 34 with respect to the average flow rate signal, so that the system does not prematurely switch from the low pressure exhalation mode to the higher pressure inhalation mode. That is, a switching setpoint offset in the positive direction from system average flow may be provided such that the system will not switch to the IPAP mode until the patient actually exerts a significant spontaneous inspiratory effort of a minimum predetermined magnitude. This will ensure that the initiation of inhalation is completely spontaneous and not forced by an artificial increase in airway pressure. A similar switching setpoint offset may be provided when in the IPAP mode to ensure the transition to the lower pressure EPAP mode will occur before the flow rate of air into the lungs of the patient reaches zero (i.e., the switch to EPAP occurs slightly before the patient ceases inhalation.) This will ensure that the patient will encounter no undue initial resistance to spontaneous exhalation.

From the above description, it will be seen that a novel method of treating sleep apnea is proposed according to which the airway pressure of the patient is maintained at a higher positive pressure during inspiration and a relatively lower pressure during expiration, all without interference with the spontaneous breathing of the patient. The described apparatus is operable to provide such treatment for sleep apnea patients by providing a flow of breathing gas to the patient at positive pressure, and varying the pressure of the air flow to provide alternately high and low pressure within the airway of the patient coordinated with the patient's spontaneous inhalation and exhalation, To provide pressure control, the flow rate of breathing gas to the patient is detected and processed to continually provide a signal which is proportional to the instantaneous breathing gas flow rate in the system. The instantaneous flow rate signal is further processed to eliminate variations attributable to normal patient respiration and other causes thus generating a signal which is proportional to the average or steady state system gas flow. The average flow signal is continually compared with the instantaneous flow signal as a means to detect the state of the patient's spontaneous breathing versus average system flow. When instantaneous flow exceeds the average flow, the patient is inhaling, and in response the pressure of gas flowing to the patient is set at a selected positive pressure, to provide a corresponding positive pressure within the airway of the patient. When comparison of the instantaneous flow rate signal with the average flow signal indicates the patient is exhaling, as for example when the instantaneous flow signal indicates flow equal to or less than the average flow, the pressure of breathing gas to the patient is adjusted to a selected lower pressure to provide a corresponding lower pressure within the airway of the patient.

Figure 2:
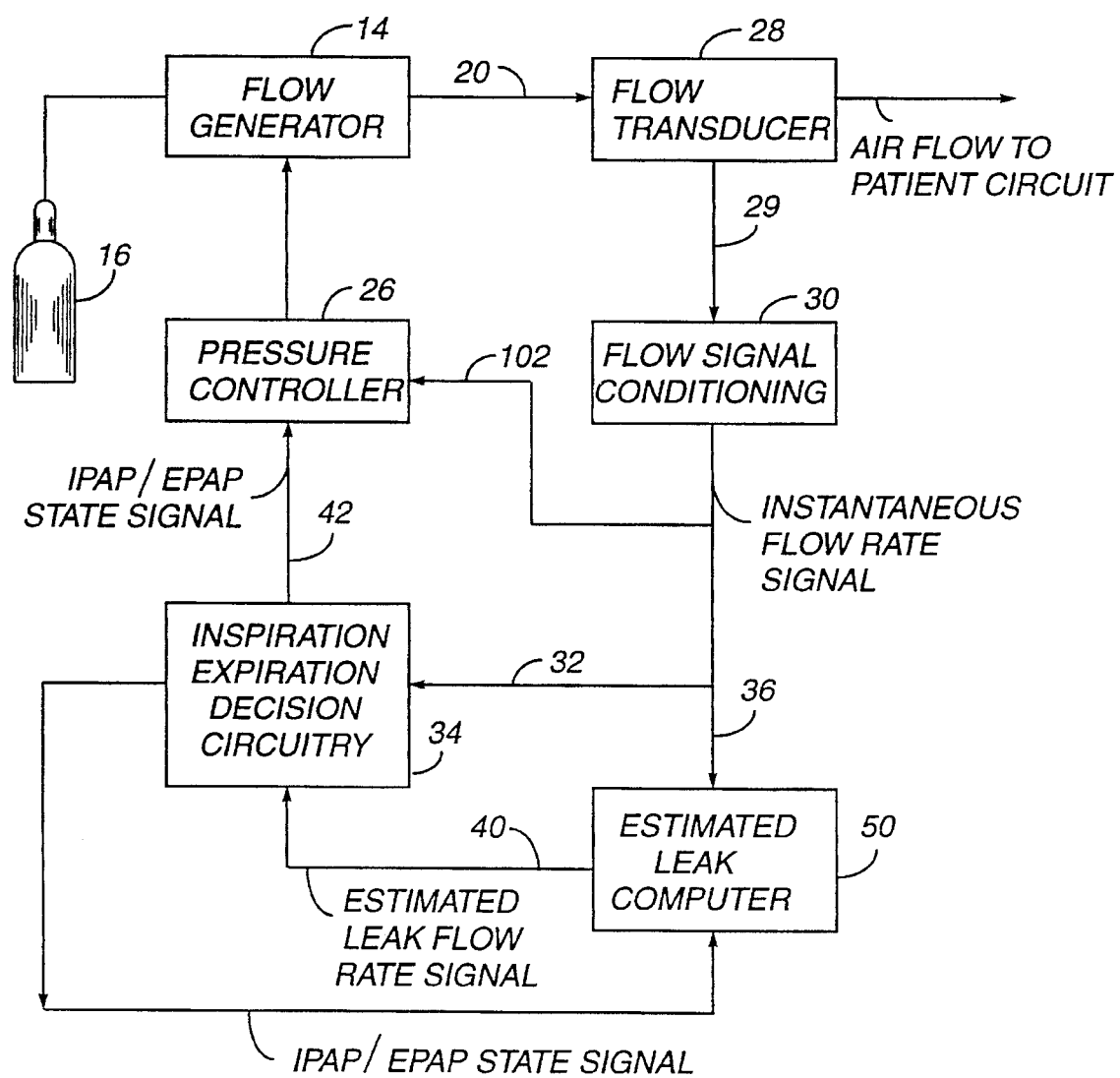
FIG. 2 is a functional block diagram showing an alternative embodiment of the invention.
Figure 3:
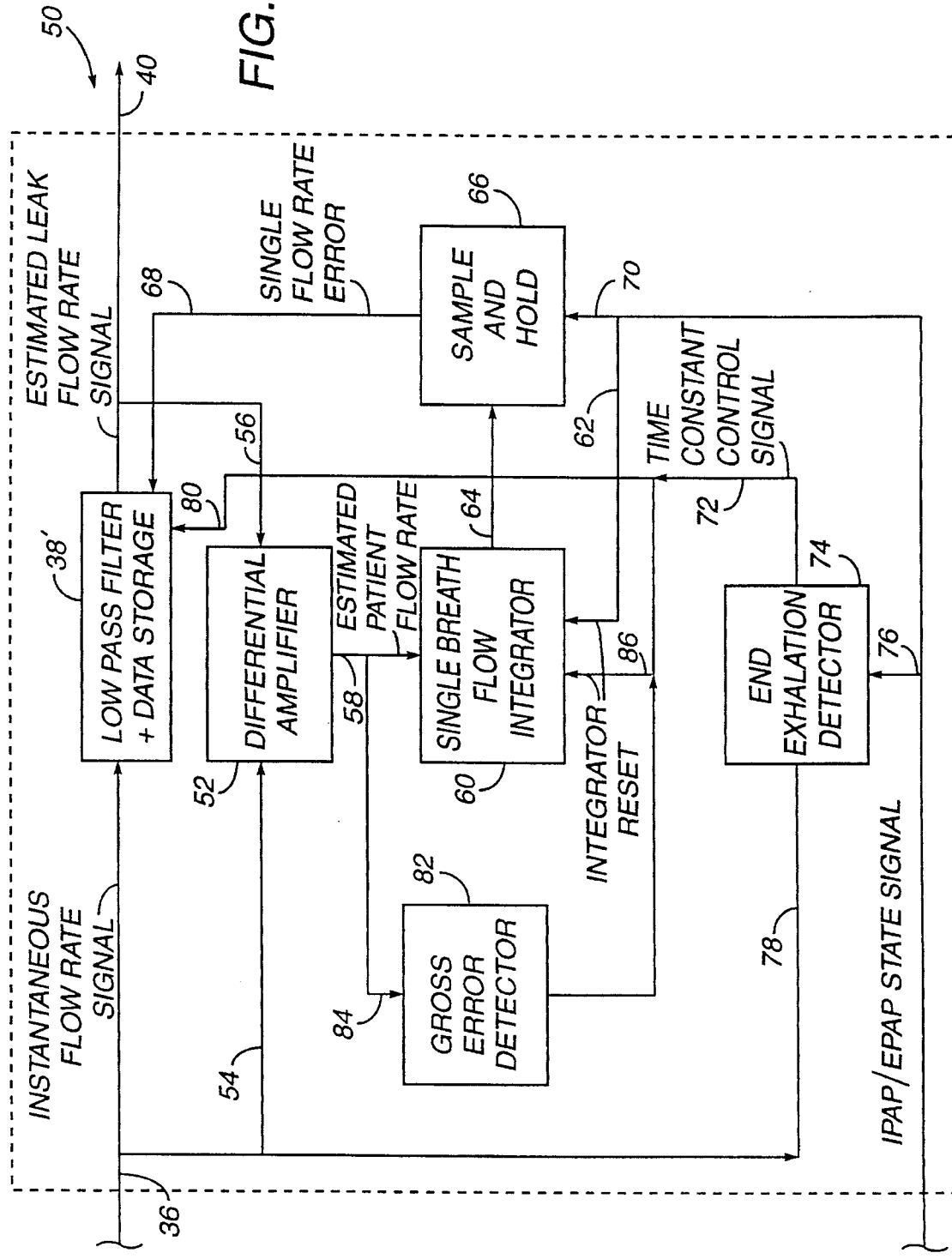
FIG. 3 is a functional block diagram of the Estimated Leak Computer of FIG. 2.

In an alternative embodiment of the invention as shown in FIGS. 2 and 3, the low pass filter 38 is replaced by an estimated leak computer which includes a low pass filter as well as other functional elements as shown in FIG. 3. The remainder of the system as shown in FIG. 2 is similar in most respects to the system shown in FIG. 1. Accordingly, like elements are identified by like numbers, and the description hereinabove of FIG. 1 embodiment also applies generally to FIG. 2.

By using the operative capability of the estimated leak computer 50, as described hereinbelow, it is possible to adjust the reference signal which is fed to decision circuitry 34 on a breath by breath basis rather than merely relying on long term average system flow. To distinguish this new reference signal from average system flow it will he referred to hereinbelow as the estimated leak flow rate signal or just the estimated leak signal.

As was noted hereinabove, the average system flow rate reference signal changes very slowly due to the long time constant of the low pass filter 38. This operative feature was intentionally incorporated to avoid disturbance of the reference signal by aberrant instantaneous flow rate signal inputs such as erratic breathing patterns. While it was possible to minimize the impact of such aberrations on the average flow rate reference signal, the average flow signal did nevertheless change, although by small increments and only very slowly in response to disturbances. Due to the long time constant of the low pass filter, such changes in the reference signal even if transitory could last for a long time.

Additionally, even a small change in the reference signal could produce a very significant effect on system triggering. For example, since the objective is to trigger the system to the IPAP mode when inhalation flow just begins to go positive, small changes in the reference signal could result in relatively large changes in the breathing effort needed to trigger the system to IPAP mode. In some instances the change in reference signal could be so great that with normal breathing effort the patient would be unable to trigger the system. For example, if the system were turned on before placement of the mask on the face of the patient, the initial free flow of air from the unattached mask could result in a very large magnitude positive value for initial average system flow. If such value were to exceed the maximum inspiratory flow rate achieved in spontaneous respiration by the patient, the system would never trigger between the IPAP and EPAP modes because the decision circuitry would never see an instantaneous flow rate signal greater than the average flow rate signal, at least not until a sufficient number of normal breathing cycles after application of the mask to the patient to bring the reference signal down to a value more closely commensurate with the actual system leak in operation. As has been noted, with the low pass filter thus could take a rather long time, during which time the patient would be breathing spontaneously against a uniform positive pressure. This would be tantamount to conventional mono-level CPAP and not at all in keeping with the present invention.

In addition to the embodiment based on a reference signal derived from estimated leak flow rate on a breath by breath basis which is controlled totally by spontaneous patient breathing, two further modes of operation also are envisioned, one being spontaneous/timed operation in which the system automatically triggers to the IPAP mode for just long enough to initiate patient inspiration if the system does not sense inspiratory effort within a selected time after exhalation begins. To accomplish this, a timer is provided which is reset at the beginning of each patient inspiration whether the inspiratory cycle was triggered spontaneously or by the timer itself. Thus, only the start of inspiration is initiated by the timer. The rest of the operating cycle in this mode is controlled by spontaneous patient breathing and the circuitry of the system to be described.

A further mode of operation is based purely on timed operation of the system rather than on spontaneous patient breathing effort, but with the timed cycles coordinated to spontaneous patient breathing.

Referring to FIG. 3, the estimated leak computer 50 includes the low pass filter 38' as well as other circuits which are operative to make corrections to the estimated leak flow rate signal based on ongoing analysis of each patient breath. A further circuit is provided which is operative to adjust the estimated leak flow rate signal quickly after major changes in system flow such as when the blower has been running prior to the time when the mask is first put on the patient, or after a major leak the system has either started or has been shut off.

The low pass filter 38' also includes a data storage capability whose function will be described hereinbelow.

The low pass filter 38' operates substantially as described above with reference to FIG. 1 in that it provides a long term average of system flow which is commensurate with steady state system leakage including the flow capacity of the exhaust port 24. This long term average is operative in the FIG. 3 embodiment to adjust the estimated leak flow rate reference signal only when system flow conditions are changing very slowly.

To provide breath by breath analysis and adjustment of the reference signal, a differential amplifier 52 receives the instantaneous flow rate signal as indicated at 54, and the estimated leak signal output from low pass filter 38' as indicated at 56.

The output of differential amplifier 52 is the difference between instantaneous flow rate and estimated leak flow rate, or, in other words, estimated instantaneous patient flow rate. This will be clear upon considering that instantaneous flow is the sum of patient flow plus actual system leakage. The estimated patient flow signal output from differential amplifier 52 is provided as indicated at 58 to a flow integrator 60 which integrates estimated patient flow breath by breath beginning and ending with the trigger to IPAP. Accordingly, an additional input to the flow integrator 60 is the IPAP/EPAP state signal as indicated at 62. The IPAP/EPAP state signal is the same as the drive signal provided to pressure controller 26; that is, it is a signal indicative of the pressure state, as between IPAP and EPAP, of the system. The state signal thus may be used to mark the beginning and end of each breath for purposes of breath by breath integration by integrator 60.

If the estimated leak flow rate signal from low pass filter 38' is equal to the true system leak flow rate, and if the patient's inhaled and exhaled volumes are identical for a given breath (i.e., total positive patient flow equals total negative patient flow for a given breath), then the integral calculated by integrator 60 will be zero and no adjustment of estimated leak flow rate will result. When the integral calculated by integrator 60 is nonzero, the integral value in the form of an output signal from integrator 60 is provided as indicated at 64 to a sample and hold module 66. Of course, even with a zero value integral, an output signal may be provided to module 66, but the ultimate result will be no adjustment of the estimated leak flow rate signal.

A nonzero integral value provided to module 66 is further provided to module 38' as indicated at 68 with each patient breath by operative action of the IPAP/EPAP state signal upon module 66 as indicated at 70. The effect of a nonzero integral value provided to module 38' is an adjustment of the estimated leak flow rate signal proportional to the integral value and in the direction which would reduce the integral value towards zero on the next breath if all other conditions remain the same.

With this system, if the patient's net breathing cycle volume is zero, and if the system leak flow rate changes, the integrator circuit will compensate for the change in leak flow rate by incremental adjustments to the estimated leak flow rate within about ten patient breaths.

The integrator circuit 60 also will adjust the estimated leak flow rate signal in response to nonzero net volume in a patient breathing cycle. It is not unusual for a patient's breathing volume to be nonzero. For example, a patient may inhale slightly more on each breath than he exhales over several breathing cycles, and then follow with a deeper or fuller exhalation. In this case, the integrator circuit would adjust the estimated leak flow rate signal as if the actual system leak rate had changed; however, since the reference signal correction is only about one tenth as large as would be required to make the total correction in one breath, the reference signal will not change appreciably over just one or two breaths. Thus, the integrator circuit accommodates both changes in system leakage and normal variations in patient breathing patterns. The integrator circuit normally would be active, for example, during rapid patient breathing.

An end exhalation module 74 is operative to calculate another data component for use in estimating the system leak flow rate as follows. The module 74 monitors the slope of the instantaneous flow rate wave form. When the slope value is near zero during exhalation (as indicated by the state signal input 76) the indication is that the flow rate is not changing. If the slope of the instantaneous flow rate signal wave form remains small after more than one second into the respiratory phase, the indication is that exhalation has ended and that the net flow rate at this point thus is the leak flow rate. However, if estimated patient flow rate is nonzero at the same time, one component of the instantaneous flow rate signal must be patient flow.

When these conditions are met, the circuit adjusts the estimated leak flow rate slowly in a direction to move estimated patient flow rate toward zero to conform to instantaneous patient flow conditions expected at the end of exhalation. The adjustment to estimated leak flow rate is provided as an output from module 74 to low pass filter 38' as indicated at 80. When this control mechanism takes effect, it disables the breath by breath volume correction capability of integrator circuit 60 for that breath only.

The output of module 74 is a time constant control signal which is provided to low pass filter 38' to temporarily shorten the time constant thereof for a sufficient period to allow the estimated leak flow rate to approach the instantaneous flow rate signal at that specific instant. It will be noted that shortening the low pass filter time constant increases the rapidity with which the low pass filter output (a system average) can adjust toward the instantaneous flow rate signal input.

Another component of estimated leak flow rate control is a gross error detector 82 which acts when the estimated patient flow rate, provided thereto as indicated at 84, is away from zero for more than about 5 seconds. Such a condition may normally occur, for example, when the flow generator 14 is running before mask 22 is applied to the patient. This part of the control system is operative to stabilize operation quickly after major changes in the leak rate occur.

In accordance with the above description, it will be seen that low pass filter 38' acts on the instantaneous flow rate signal to provide an output corresponding to average system flow, which is system leakage since patient inspiration and expiration over time constitutes a net positive flow of zero. With other enhancements, as described, the system average flow can be viewed as an estimate of leakage flow rate.

The differential amplifier 52 processes the instantaneous flow rate signal and the estimated leak flow rate signal to provide an estimated patient flow rate signal which is integrated and nonzero values of the integral are fed back to module 38' to adjust the estimated leak flow rate signal on a breath by breath basis. The integrator 60 is reset by the IPAP/EPAP state signal via connection 62.

Two circuits are provided which can override the integrator circuit, including end exhalation detector 74 which provides an output to adjust the time constant of low pass filter 38' and which also is provided as indicated at 86 to reset integrator 60. Gross error detector 82 is also provided to process estimated patient flow rate and to provide an adjustment to estimated leak flow rate under conditions as specified. The output of module 82 also is utilized as an integrator reset signal as indicated at 86. It will be noted that the integrator 60 is reset with each breath of the patient if, during that breath, it is ultimately overridden by module 74 or 82. Accordingly, the multiple reset capabilities for integrator 60 as described are required.

In operation, the system may be utilized in a spontaneous or bi-level triggering mode, a spontaneous/ timed or bi-level/timed (bi-level/T) mode or a purely timed mode of operation. In spontaneous operation, decision circuitry 34 continuously compares the instantaneous flow rate with estimated leak flow rate. If the system is in the EPAP state or mode, it remains there until instantaneous flow rate exceeds estimated leak flow rate by approximately 40 cc per second. When this transition occurs, decision circuitry 34 triggers the system into the IPAP mode for 150 milliseconds. The system will then normally remain in the IPAP mode as the instantaneous flow rate to the patient will continue to increase during inhalation due to spontaneous patient effort and the assistance of the increased IPAP pressure.

After the transition to the IPAP mode in each breath, a temporary offset is added to the estimated leak flow rate reference signal. The offset is proportional to the integral of estimated patient flow rate beginning at initiation of the inspiratory breath so that it gradually increases with time during inspiration at a rate proportional to the patient's inspiratory flow rate. Accordingly, the flow rate level above estimated leak flow needed to keep the system in the IPAP mode during inhalation decreases with time from the beginning of inhalation and in proportion to the inspiratory flow rate. With this enhancement, the longer an inhalation cycle continues, the larger is the reference signal below which instantaneous flow would have to decrease in order to trigger the EPAP mode. For example, if a patient inhales at constant 500 cc per second until near the end of inspiration, a transition to EPAP will occur when his flow rate drops to about 167 cc per second after one second, or 333 cc per second after two seconds, or 500 cc per second after three seconds, and so forth. For a patient inhaling at a constant 250 cc per second, the triggers would occur at 83, 167 and 250 cc per second at one, two and three seconds into IPAP, respectively.

In this way, the EPAP trigger threshold comes up to meet the inspiratory flow rate with the following benefits. First, it becomes easier and easier to end the inspiration cycle with increasing time into the cycle. Second, if a leak develops which causes an increase in instantaneous flow sufficient to trigger the system into the IPAP mode, this system will automatically trigger back to the EPAP mode after about 3.0 seconds regardless of patient breathing effort. This would allow the volume-based leak correction circuit (i.e., integrator 60) to act as it is activated with each transition to the IPAP mode. Thus, if a leak develops suddenly, there will be a tendency toward automatic triggering rather than spontaneous operation for a few breaths, but the circuit will not be locked into the IPAP mode.

Upon switching back to the EPAP mode, the trigger threshold will remain above the estimated leak flow rate approximately 500 milliseconds to allow the system to remain stable in the EPAP mode without switching again while the respective flow rates are changing. After 500 milliseconds, the trigger threshold offset is reset to zero to await the next inspiratory effort.

The normal state for the circuit is for it to remain in the EPAP mode until an inspiratory effort is made by the patient. The automatic corrections and adjustments to the reference signal are effective to keep the system from locking up in the IPAP mode and to prevent auto-triggering while at the same time providing a high level of sensitivity to inspiratory effort and rapid adjustment for changing leak conditions and breathing patterns.

In the spontaneous/timed mode of operation, the system performs exactly as above described with reference to spontaneous operation, except that it allows selection of a minimum breathing rate to be superimposed upon the spontaneous operating mode. If the patient does not make an inspiratory effort within a predetermined time, the system will automatically trigger to the IPAP mode for 200 milliseconds. The increased airway pressure for this 200 milliseconds will initiate patient inspiration and provide sufficient time that spontaneous patient flow will exceed the reference signal so that the rest of the cycle may continue in the spontaneous mode as above described. The breaths per minute timer is reset by each trigger to IPAP whether the transition was triggered by the patient or by the timer itself.

In the timed operating mode, all triggering between IPAP and EPAP modes is controlled by a timer with a breath per minute control being used to select a desired breathing rate from, for example, 3 to 30 breaths per minute. If feasible, the selected breathing rate is coordinated to the patients spontaneous breathing rate. The percent IPAP control is used to set the fraction of each breathing cycle to be spent in the IPAP mode, For example, if the breaths per minute control is set to 10 breaths per minute (6 seconds per breath) and the percent IPAP control is set to 33%, then the flow generator will spend, in each breathing cycle, two seconds in IPAP and four seconds in EPAP.

Figure 4:
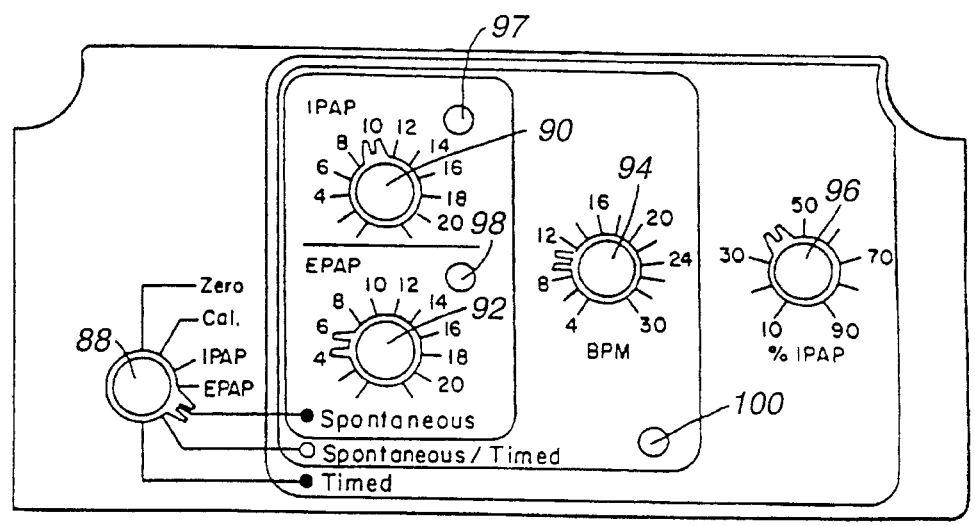
FIG. 4 is a frontal elevation of a control panel for a first embodiment of the apparatus of this invention.

FIG. 4 illustrates a control panel for controlling the system above described and including a function selector switch 88 which includes function settings for the three operating modes, namely, spontaneous (or bi-level), spontaneous/timed (or bi-level/ timed), and timed, as above described. The controls for spontaneous mode operation include IPAP and EPAP pressure adjustment controls 90 and 92, respectively. These are used for setting the respective IPAP and EPAP pressure levels. In the spontaneous/timed mode of operation, controls 90 and 92 are utilized as before to set IPAP and EPAP pressure levels, and breaths per minute control 94 additionally is used to set the minimum desired breathing rate in breaths per minute. In the timed mode of operation, controls 90, 92 and 94 are effective, and in addition the per cent IPAP control 96 is used to set the time percentage of each breath to be spent in the IPAP mode.

Lighted indicators such as LED's 97, 98 and 100 are also provided to indicate whether the system is in the IPAP or EPAP state, and to indicate whether, in the spontaneous/ timed (bi-level/timed) mode of operation, the instantaneous state of the system is spontaneous operation or timed operation.

Additionally, it may be desirable to provide a flow compensation signal to pressure controller 26 as indicated at 102 in FIG. 2 to compensate for flow resistance inherent in the circuit; a non-rebreathing valve may be utilized in lieu of exhaust port 24 at mask 22, and the like.

Figure 5:
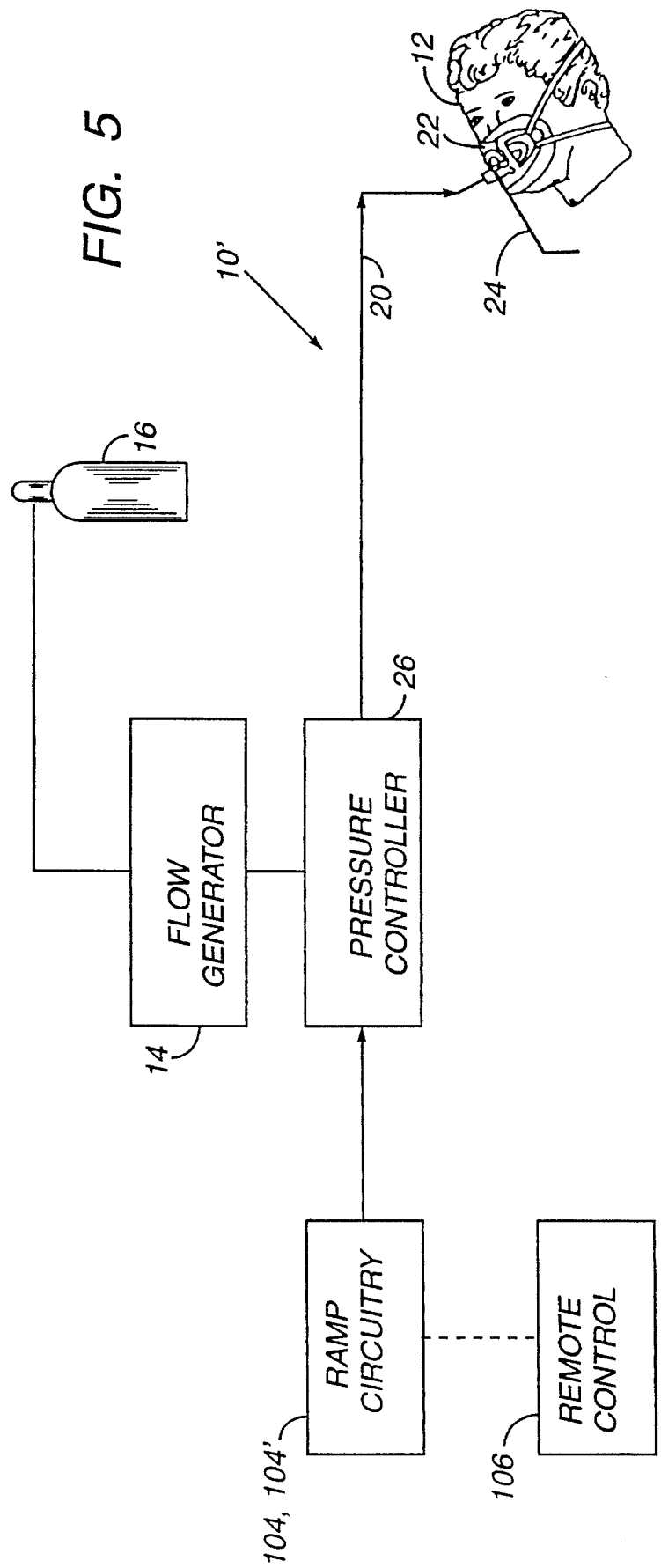
FIG. 5 is a functional block diagram of a further embodiment of an apparatus according to the instant invention.
Figure 7A:
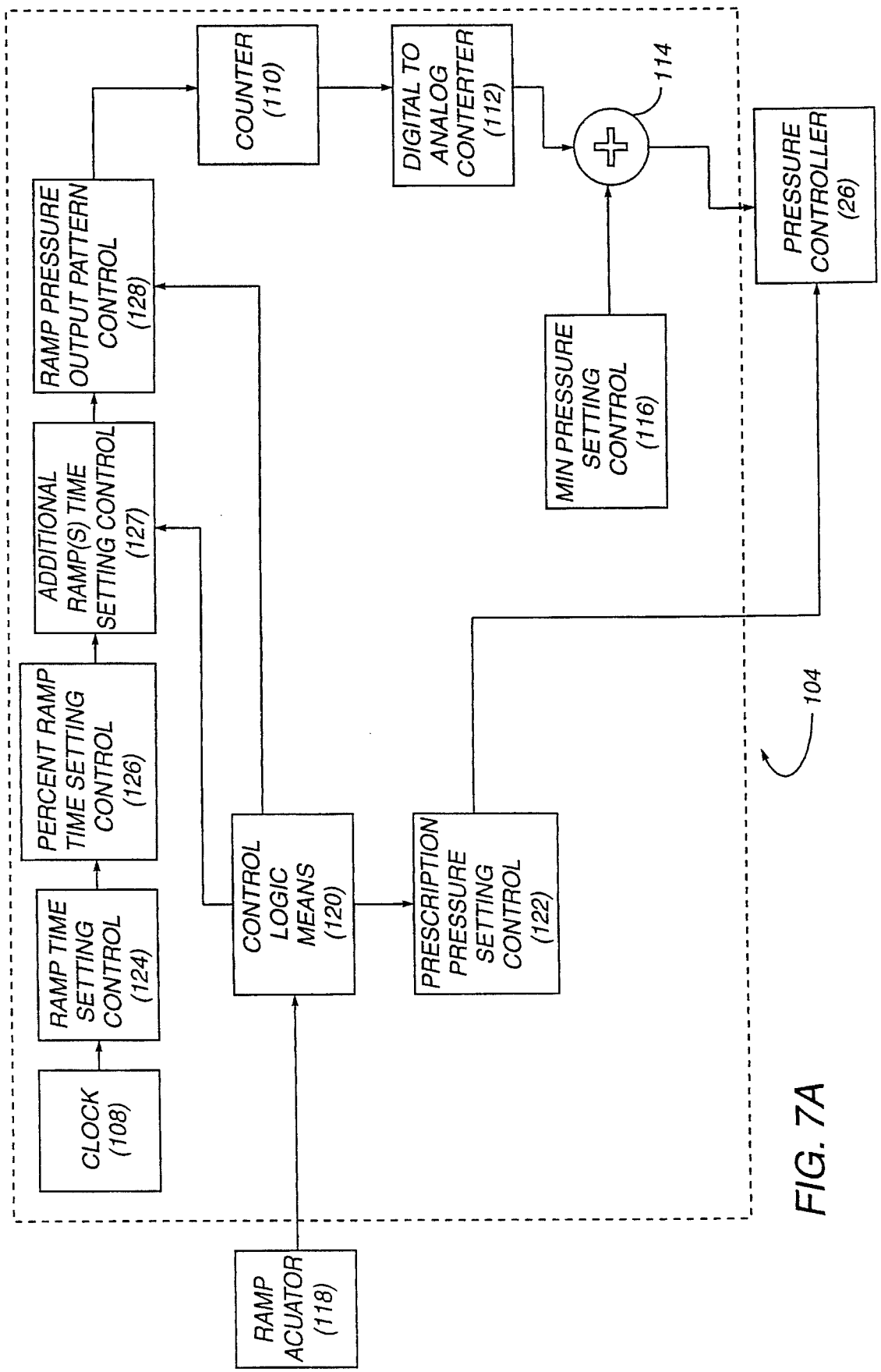
FIG. 7A is a flow diagram of a first embodiment of programmable ramp control circuitry of the instant invention suitable for use in respiratory system ventilation apparatus.
Figure 7B:
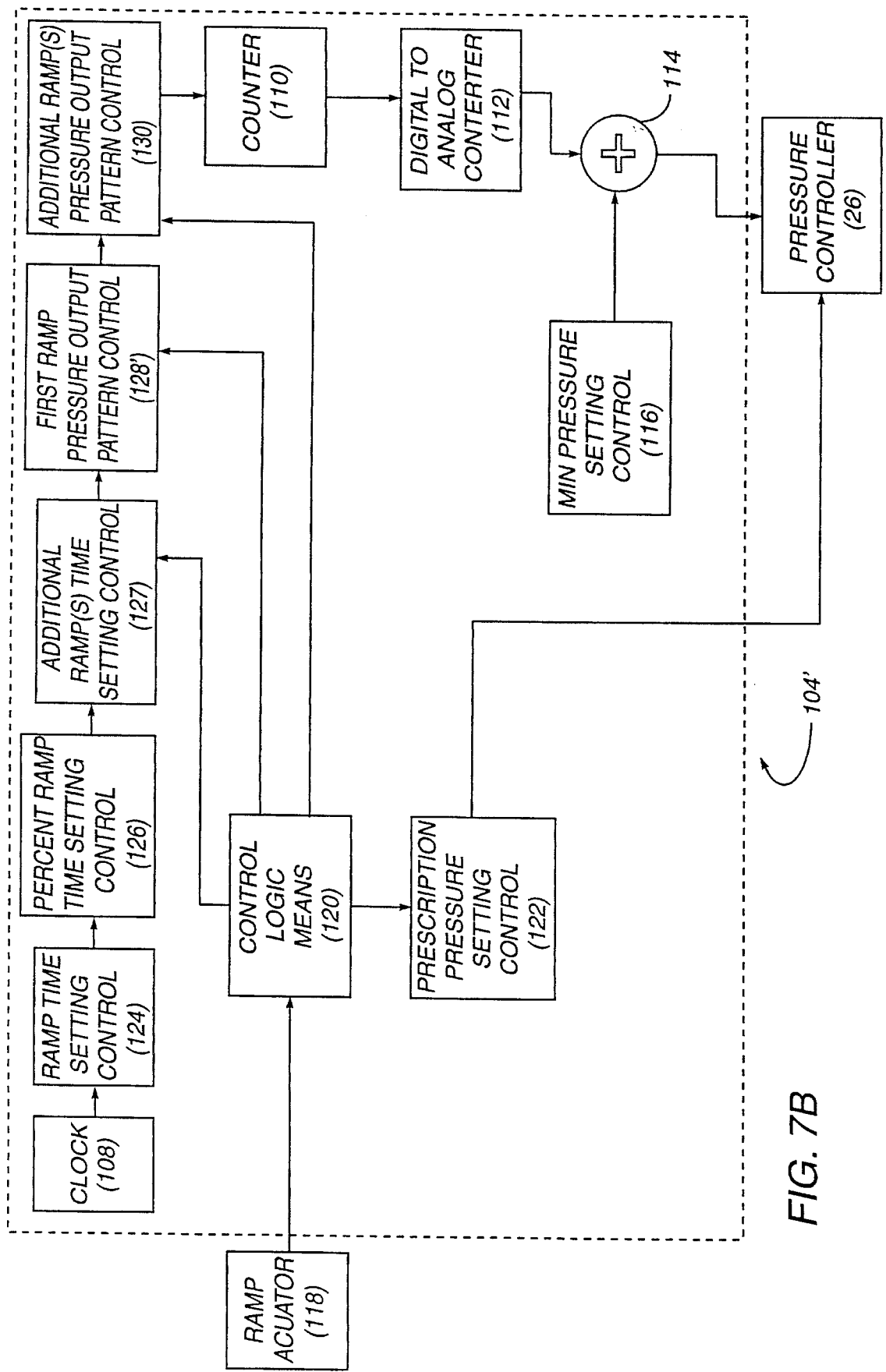
FIG. 7B is a flow diagram of a further embodiment of programmable ramp control circuitry of the instant invention suitable for use in respiratory system ventilation apparatus.

Turning to FIG. 5, there is depicted a further embodiment of the present invention, herein designated by reference numeral 10'. This embodiment functions substantially as a mono-level CPAP apparatus wherein the pressures of the breathing gas flow supplied to the patients airway is substantially constant except when ramp control circuitry means 104 or 104', described below in connection with FIGS. 7A and 7B, is activated by the patient, through manipulation of a suitable mechanical actuator such as a switch, a button, or the like, provided on the housing of the apparatus 10' or on remote control 106 to produce one or more output pressure "ramp cycles." As will be later described in greater detail, remote control 106 may also be operable to turn apparatus 10 "ON" and "OFF."

FIG. 5A illustrates alternative means for effecting selective activation of the aforesaid ramp cycles. Desirably, the alternative ramp activation means may comprise any suitable sensor means for detecting and responding to predetermined signals consciously produced by the patient. In this regard, according to a presently preferred construction, the ramp activation means comprises a sensor means 106' in the form of a pressure transducer responsive to a pressure or pressures of selected magnitude and/or frequency. For instance, the pressure transducer may be a microphone located within or proximate the gas flow system or breathing circuit (i.e., in or near the patient's respiratory interface, associated gas flow conduit or gas flow generator) and capable of detecting sound waves of a limited frequency range substantially spanning that associated with human speech. Constructed and arranged as such, the transducer would be nonresponsive to common ambient sounds produced by the patient (e.g., coughing or sneezing), machinery noise, music or animal sounds. Moreover, by being isolated through its enclosure within the gas flow system, the transducer would detect only the patient's speech to the exclusion of others in the vicinity or speech emanating from television or radio sources. Upon detection of the patient's speech such as, for example, when the patient awakens and then speaks to initiate a new ramp cycle to facilitate transition to a sleeping state, the transducer generates and transmits an activation signal to the ramp circuitry 104,104' to initiate the desired ramp cycle. The ramp activation sensor may alternatively be operable to begin a ramp cycle in response to detection of a predetermined pattern of inhalations and/or exhalations or other conscious actions by the patient.

As a variant to a manually manipulable remote control power actuator, apparatus 10' may instead include an automatic "ON/OFF" mechanism to achieve the same result. According to a presently preferred construction, such mechanism may comprise a sensor means situated within or proximate the patient's breathing circuit which circuit (as noted above) comprises gas conduit 20, gas flow generator means 14 and a suitable respiratory interface such as mask 22. This sensor means functions as a patient presence sensor and is identified by reference numeral 107'. The "patient sensor means" sensor 107' may suitably assume the form of a pressure, flow, thermal, audio, optic, electrical current, voltage, force or displacement transducer which detects the presence (and/or absence) of the patient. More particularly, according to a first mode of operation, when the respiratory interface is appropriately positioned over the patient's face, the sensor will operate to detect the patient's presence and generate a signal that is transmitted to the flow generator 14 to activate the apparatus. In a second modality, the patient sensor means may function exclusively to deactivate the apparatus. Hence, upon removal of the respiratory interface, the sensor would fail to detect any conditions indicative of the patient's presence and, therefore, generate and transmit an appropriate signal to deactivate the apparatus. A third mode of operation combines these functions. In other words, the patient sensor means 107' may be operable to detect both the presence and absence of the patient and generate a signal to activate the apparatus upon detection of a condition indicative of the patient's presence, as well as an apparatus deactivation signal upon failure of detecting such a condition, i.e., the patient's absence.

The embodiment of the instant invention illustrated in FIG. 6 operates much like the embodiment revealed in FIG. 1, i.e., a bi-level apparatus. Apparatus 10", however, like apparatus 10' shown in FIG. 5, also includes remote control 106 and ramp control circuitry means 104 or 104'. It will be understood that in lieu of remote control 106 apparatus 10" may utilize a sensor means 106', e.g., a pressure transducer similar to the pressure transducer 106' described with respect to FIG. 5A, for the purpose of ramp cycle activation. In addition, it will also be understood that if the remote control 106 is eliminated, the apparatus may be activated and deactivated by appropriate signals generated by suitable means such as patient sensor means 107' which are then transmitted therefrom to the flow generator 14 as was also discussed in connection with FIG. 5A.

According to the preferred embodiments, the ramp control circuitry means 104 (FIG. 7A) or 104' (FIG. 7B) provides full prescription pressure on apparatus activation or "start up" and controls the parameters of magnitude, duration and pressure output pattern or "shape" of both the initial ramp cycle and any additional ramp cycles. Unlike other apparatus having ramp capability wherein a ramp cycle automatically commences upon apparatus start up, apparatus 10' or 10" incorporating ramp control circuitry means 104 or 104' outputs pressure at full prescription pressure (which is preset by the patient's overseeing health care professional) until conscious activation of the initial ramp cycle by the patient. This allows the patient to check for system leaks immediately following start up. Alternatively, ramp control circuitry means 104 or 104' may be configured with suitable signal detection means whereby it automatically commences a ramp cycle either upon apparatus startup, after a preset delay, or upon detection of a substantially stabilized average system leakage signal from low pass filter 38 (FIG. 2) or a substantially stabilized estimated leak flow rate signal from estimated leak computer 50 (FIG. 3) following placement of mask 22 on the patient's face. The commonality to all embodiments of the ramp control circuitry means being, however, that at least those ramp cycles subsequent to initial ramp cycle be selectively activatable by the patient via means to be described hereinbelow. As will be more fully appreciated from the following, the apparatus 10' or 10" equipped with ramp control circuitry means 104 or 104' permits the patient to not only control the aforesaid parameters of the ramp cycles (which, to provide optimum treatment effectiveness may need to be adjusted daily) but the commencement times of the ramp cycles as well.

Turning first to FIG. 7A the ramp cycles produced by the ramp control circuitry means 104 are generated by using a clock 108 to drive a counter 110. The counter 110 increments for each rising edge of the clock 108 and the output of the counter, which is influenced by a number of factors described hereinafter, is transmitted to a digital to analog converter 112. Other suitable means, however, such as a microprocessor may be used in place of digital to analog convertor 112 if desired. The analog output of the converter is added at juncture 114 to the minimum pressure setting that is input via an adjustable minimum pressure setting control 116 and thereafter transmitted to the pressure controller 26 to provide a pressure ramp cycle. Minimum pressure setting control 116 is operable to establish a minimum ramp pressure of zero or greater for ramping of standard CPAP and ramping of IPAP and/or EPAP in bi-level respiratory therapy.

As mentioned hereinabove as an alternative to sensor means 106', a ramp actuator 118, typically a user-manipulable button, switch, or the like, may be operated to effect commencement of a ramp cycle, whether such cycle be the initial or a subsequent cycle. One such ramp actuator is desirably provided on both the apparatus 10' or 10" and the remote control 106. A similar arrangement may also be employed for the apparatus power "ON/OFF" actuator. Whether provided on the remote control or apparatus 10' or 10" it is preferred that the power actuator (not shown) be substantially different in physical configuration than that of the ramp actuator such that a patient is provided visual and tactile feedback and can readily and reliably identify and operate the actuators either by sight or sense of touch. For purposes of illustration, both the power actuator and ramp actuator will be understood to be depressible buttons; however, their possible physical manifestations are not intended nor should they be construed to be limited exclusively thereto. Upon depression of the power actuator button, a control logic means 120 selects the patient's prescription pressure as determined by the patient's sleep study as the start-up pressure. The prescription pressure is initially input by the physician or other health care professional into the ramp control circuitry means 104 via a prescription pressure setting control 122 which permits establishment and subsequent adjustment of the magnitude of the prescription pressure. The expression "prescription pressure" in the present context meaning, of course, a single prescription pressure in the case of standard mono-level CPAP therapy and a bifurcated prescription pressure (IPAP and EPAP) in respect to bi-level therapy. A ramp time setting control 124 such as, for example, a rotary switch or other suitable control, is also provided (preferably internally of the apparatus housing to prevent patient tampering) and it, too, is normally set by the health care professional to establish the appropriate ramp time of the first ramp cycle of the apparatus 10' or 10", i.e., that ramp cycle which is employed when a patient first seeks to fall asleep, such as at bed time. The appropriate ramp time for the first ramp cycle is also determined from data gathered in connection with the patient's sleep study. A typical duration or "ramp time" of the initial ramp cycle may be up to as high as 45 minutes or even longer.

As the patient becomes gradually accustomed to using the apparatus and/or realizes benefits from the therapy, it is common for the patient to require less time to initially fall asleep when using the apparatus than when the patient first began treatment. Consequently, when using any apparatus equipped with the ramp control circuitry means of the present invention, a need occasionally arises for the initial ramp time setting to be adjusted (typically to a lesser duration than that initially set by the health care professional). Since it is often times inconvenient or impractical for the patient to meet with his or her health care professional for necessary readjustments of the ramp time setting control 124, the ramp control circuitry means of the present invention further desirably comprises a percent ramp time setting control 126 that is accessible by the patient and adjustable to produce for the initial ramp cycle a modified initial ramp time that is a fraction of the initial ramp time last established by the health care professional via ramp time setting control 124. Percent ramp time setting control 126, preferably a rotary switch or the like, is adjustable to produce initial ramp times ranging from a minimum of from about 0 to 20% up to and including a maximum of 100% of the initial ramp time preset by the health care professional.

Frequently, a patient awakens during a period of extended sleep for any number of reasons. And, as is generally the case, the time required for a patient to fall back to sleep once awakened is less than that initially required. To accommodate this particular phenomenon, the ramp control circuitry means 104 (and 104' of FIG. 7B) of the present invention preferably include an additional ramp(s) time setting control 127 that is adjustable to produce in ramp cycles subsequent to the initial ramp cycle (the duration of which is established by the setting of control 124 as modified by the setting of control 126) ramp times ranging from a minimum of from about 0 to 20% of the initial ramp cycle time up to and including a maximum of 100% of the initial ramp cycle time. The ramp circuitry control means 104 and 104' are thus designed such that upon activation of any ramp cycle subsequent to the initial ramp cycle the apparatus 10' or 10" executes a ramp cycle lasting for a duration established by the setting of the additional ramp(s) time setting control 127. Hence, the patient is not only assisted in falling back to sleep by the gradual increase in pressure but also is more quickly treated by the beneficial prescription pressure once he does again fall asleep due to the generally shorter duration of the subsequent ramp cycle(s) relative to the initial ramp cycle. The additional ramp(s) time setting control 127 is preferably readily accessible by the patient yet not in area where it is likely to be inadvertently bumped or changed.

Looking to FIG. 7A, it is revealed that the ramp control circuitry means 104 also preferably include an adjustable ramp pressure output pattern control 128 for establishing a predetermined pattern of pressure output from pressure controller 26 during progression in a ramp cycle from the minimum ramp pressure set by minimum pressure setting control 116 and the maximum ramp pressure (prescription pressure) set by the prescription pressure setting control 122. In FIG. 7B, the virtual structural and functional equivalent of ramp pressure output pattern control 128 is the first ramp pressure output pattern control 128'. Either of controls 128 or 128' are operable by the health care professional or the patient to establish the selected pattern by which the pressure controller 26 outputs pressurized air during any ramp cycle in the case of ramp control circuitry means 104 or during the first ramp cycle in the case of ramp control circuitry means 104'. Thus, the controls 128 and 128' serve to establish the "shape" of the ramp curve as a function of output pressure versus ramp time. Because of controls 128 and 128', essentially any desired pattern of ramp output pressure may be selected, examples of which will be discussed later by reference to FIGS. 8A, 8B and 8C. In further connection therewith, ramp circuitry control means 104' of FIG. 7B is distinguished from ramp circuitry control means 104 of FIG. 7A by virtue of an adjustable component identified as additional ramp(s) pressure output pattern control 130. The function of this particular control is to enable an operator to form the pressure output pattern of ramp cycles subsequent to the initial ramp cycle into a pattern different therefrom. To illustrate, the initial ramp pattern established by the first ramp pressure output pattern control 128' may be, for example, substantially linear in slope, whereas the subsequent ramp pattern established by the additional ramp(s) pressure output pattern control 130 may be, inter alia, curvilinear or stepped in slope. The first ramp pressure output pattern controls 128,128' as well as the additional ramp(s) pressure output pattern control 130 are adjustable to select patterns of the initial and subsequent pressure ramps for standard mono-level CPAP and for IPAP and EPAP in bi-level CPAP treatment.

The operation of ramp circuitry control means 104 is essentially as follows. Once the apparatus 10' or 10" within which means 104 is incorporated is powered and discharging pressurized air at prescription pressure, a first depression of ramp actuator button 118 (or detection by sensor means 106' of predetermined signals consciously produced by the patient) results in transmission of a signal to control logic means 120 causing the control logic means to commence a first ramp cycle. When activated, the first ramp cycle effects a drop in output pressure to the minimum pressure setting determined by the position of minimum pressure setting control 116 (typically approximately 2.5 cm $H_2O$) over a period of up to 5 seconds (normal motor-blower run down). Upon reaching the minimum pressure, the output pressure from pressure controller 26 begins to increase and continues to increase for the period of time assigned by the ramp time setting control 124 as modified by percent ramp control 126 in accordance with the predetermined pattern dictated by the ramp pressure output control 128 until the prescription pressure is attained. Thereafter, the output pressure remains at the prescription pressure in the mono-level apparatus 10' depicted in FIG. 5, while in bi-level apparatus 10" shown in FIG. 6 the prescription pressure fluctuates between the IPAP and EPAP pressures.

Upon a second or any subsequent depression of the ramp actuator button 118 (or subsequent detection of predetermined signals by sensor means 106') there is transmitted to the control logic means 120 a signal directing same to commence another ramp cycle whose duration is determined not only by the setting of the ramp time setting control 124 and percent ramp time setting control 126 but also by that of the additional ramp(s) time setting control 127, the influence of such control 127 being selectively overridden by control logic means 120 during the initial ramp cycle. It will be appreciated that the pattern or shape of the pressure output curve of any additional ramp cycle is determined by the setting of ramp pressure output pattern control 128 except that such pattern will be compressed in proportion to the fraction of the initial ramp time chosen by the setting of the additional ramp(s) time setting control 127.

The ramp control circuitry means 104' illustrated in 7B operates essentially identically to its counterpart of FIG. 7A, the primary difference being that ramp control circuitry means 104', via the additional ramp(s) pressure output pattern control 130, enables the pressure pattern of the second and any other additional ramp cycles to differ from that of the initial ramp cycle. As an example, where the first ramp pressure output pattern control 128' may be adjusted so as to produce a substantially linear slope output pressure pattern, the additional ramp(s) pressure output pattern control 130 may be selectively adjusted so as produce a stepped, curved or still other pressure output pattern different from the substantially linear slope of the first ramp cycle, as may be desired or necessary.

Figure 8A:
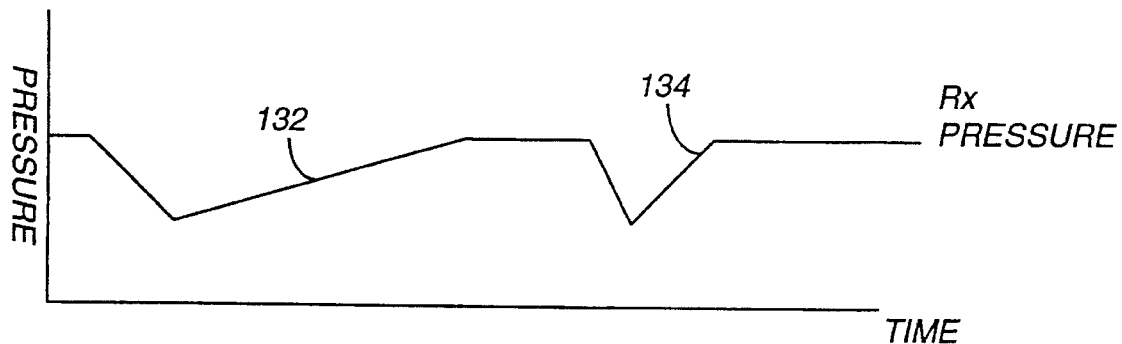
FIGS. 8A, 8B and 8C reveal three examples of typical ramp curve shapes that may be achieved via the programmable ramp circuitry of FIG. 7.
Figure 8B:
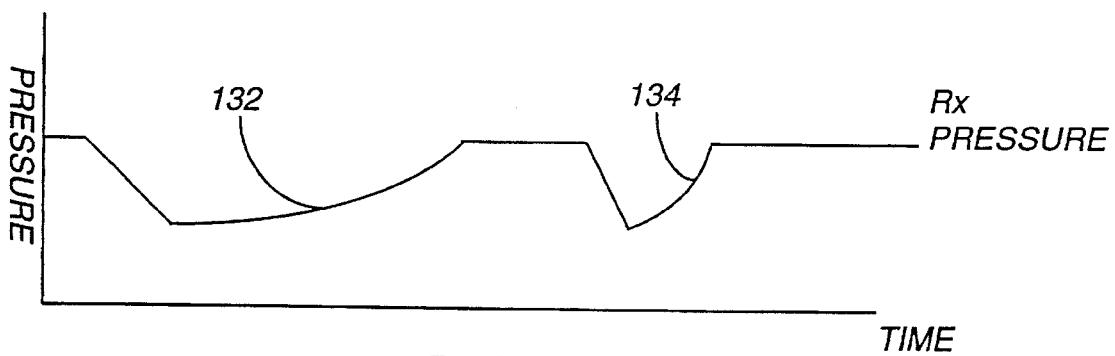
Figure 8C:
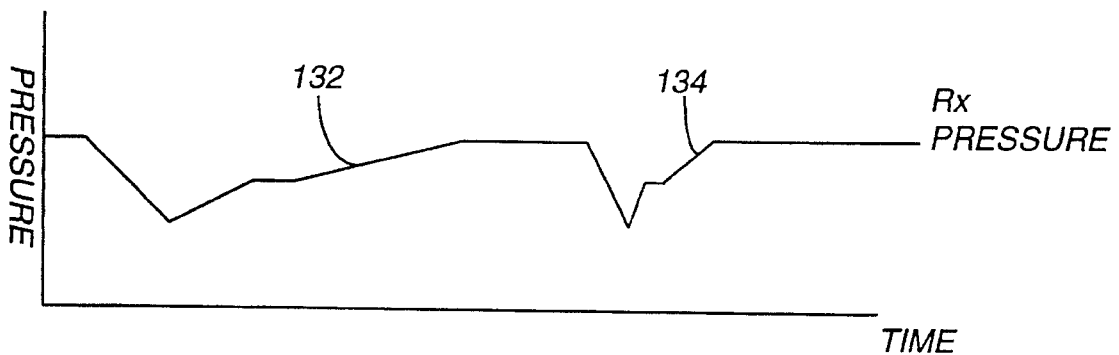

FIG. 8A, 8B and 8C reveal exemplary shapes of pressure output patterns which may be selected for the first 132 and subsequent 134 ramp cycles, namely, substantially linear slope in FIG. 8A, curvilinear in FIG. 8B and stepped in FIG. 8C. It will be appreciated that the pressure output patterns may assume virtually any desired configuration to best suit a particular patient's requirements and, as noted hereabove, the second and subsequent ramp patterns may differ from their associated initial ramp cycles.

Figure 9A:
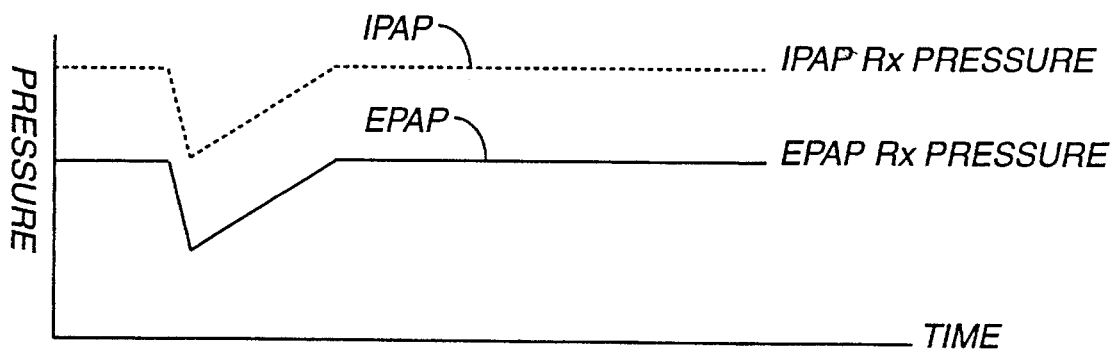
FIGS. 9A, 9B, 9C, 9D, 9E and 9F illustrate representative IPAP and EPAP ramping operations.
Figure 9B:
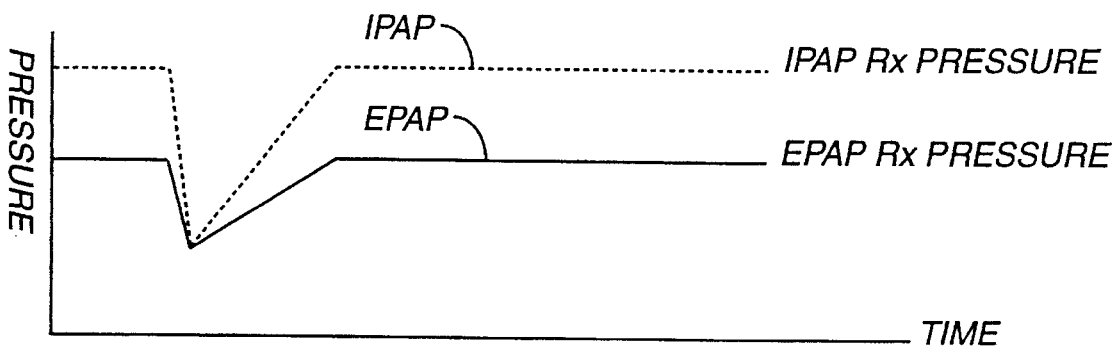
Figure 9C:
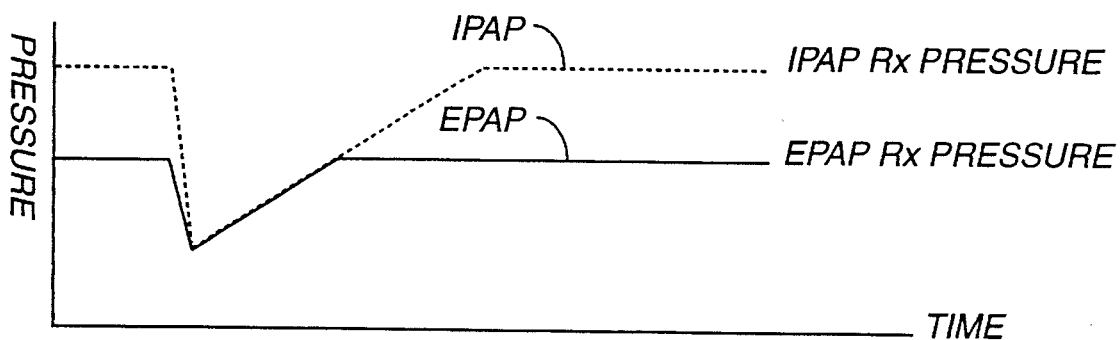
Figure 9D:
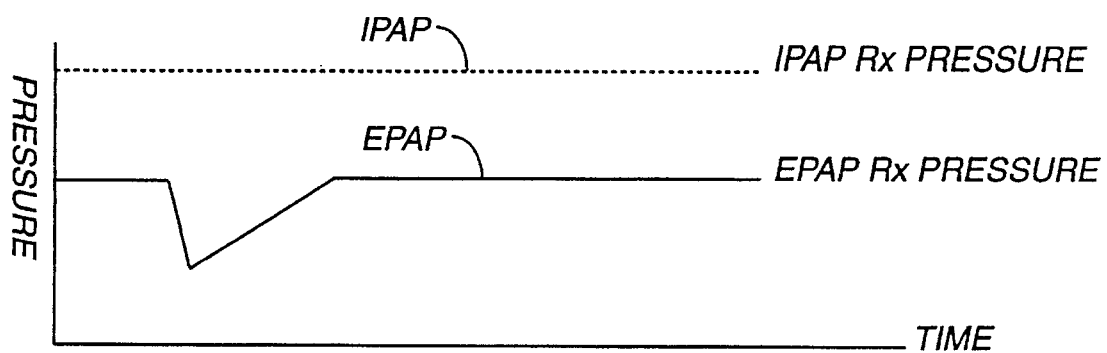
Figure 9E:
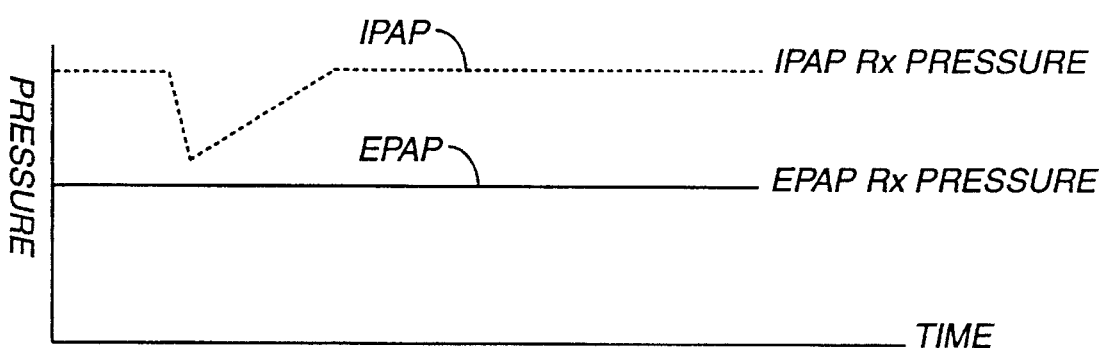
Figure 9F:
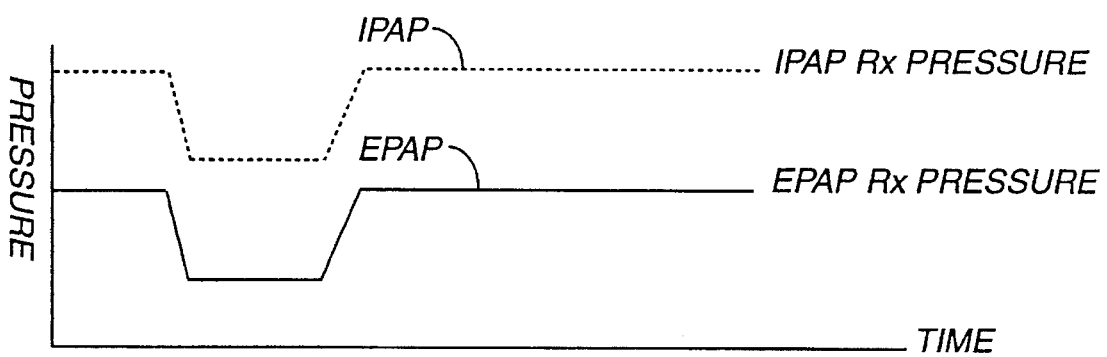

While not exhaustively illustrated to depict all possible scenarios, FIGS. 9A, 9B, 9C, 9D, 9E and 9F are included to show a representative sampling of IPAP and EPAP ramping operations in bi-level therapy which are achievable through appropriate utilization of ramp control circuitry means 104, 104'. For instance, FIG. 9A graphically shows a situation where the relative ramp shapes, magnitudes and durations of the IPAP and EPAP ramps are identical and simultaneous. Although their minimum ramp pressures differ. FIG. 9B reflects a condition wherein the IPAP and EPAP ramps have the same minimum pressure value and duration but differ in shape or slope. FIG. 9C represents IPAP and EPAP ramps having equal minimum ramp pressures and slopes but different durations. In FIG. 9D only EPAP is ramped and in FIG. 9E only IPAP is ramped. FIG. 9F possesses characteristic traits of both FIGS. 9A and 8C. That is, similar to those shown in FIG. 9A, the relative ramp shapes, magnitudes and durations of the IPAP and EPAP ramps are identical and simultaneous. And, like the ramp configurations of FIG. 8C, the ramps of FIG. 9F also include stepped portions, although the generally steady-pressure step is located at the beginning rather than at an intermediate stage of the ramp cycle. Other relative IPAP and EPAP ramp arrangements will be readily appreciated by those skilled in the subject art. Hence, the ramp curves shown in FIGS. 9A–9F should merely be viewed as illustrative but not limitative of the feasible configurations of IPAP and EPAP ramps considered to be within the operational capacities of the ramp control circuitry means 104,104'. Furthermore, it will also be understood that the IPAP and EPAP ramp configurations displayed in FIGS. 9A–9F are not representative of any specific ramp cycle. Thus, theirs and related ramp cycles may be incorporated into the first and/or any subsequent ramp cycles.

FIGS. 10 through 15 bring to light additional features and embodiments of the present invention. Although the various system control circuits disclosed therein are depicted for illustrative purposes as being used in conjunction with a feedback type positive airway pressure ventilation apparatus (in part because they are well suited to the particular operational characteristics of such apparatus), it will be understood that the control circuits disclosed in these figures (or their equivalents) may also be incorporated into non-feedback type mono-level, bi-level and variable positive airway pressure apparatus generally of the kinds described hereinabove.

Figure 10:
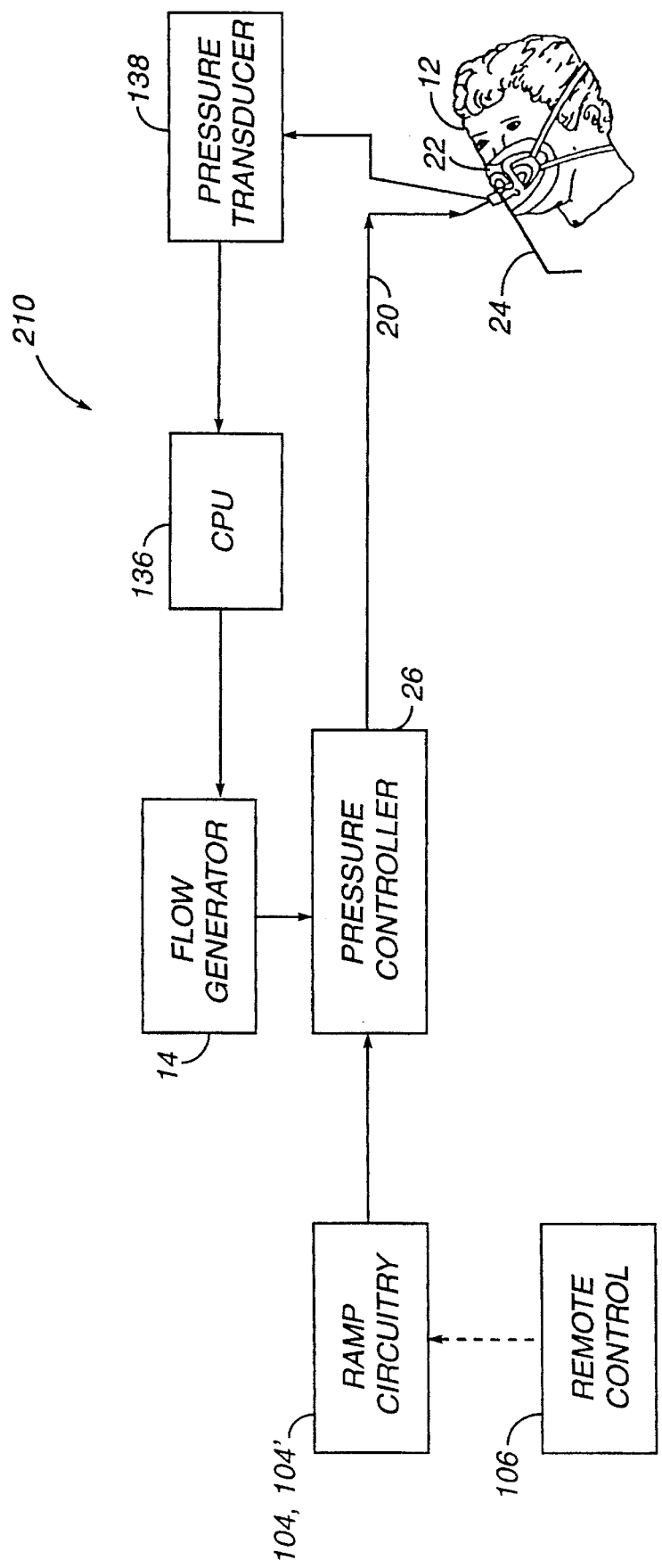
FIG. 10 is a functional block diagram of a further embodiment of an apparatus according to the instant invention.

Turning to FIG. 10, where like references represent elements similar to those thus far discussed (as is also the case in the remaining views), there is generally indicated by reference numeral 210 a functional block diagram of a feedback-type positive airway pressure ventilation apparatus which constitutes another presently preferred embodiment of the instant invention. The general characteristics of the feedback circuit portion of the apparatus 210 is, per se, known in the art; see, for example, U.S. Pat. No. 5,199,424. Moreover, the essential components of the feedback circuit are common to FIGS. 10 through 15 and the following structural and functional description of such circuit is applicable to FIGS. 11 through 15 as well as to FIG. 10.

Like all embodiments heretofore described, apparatus 210 includes a motor driven flow generator 14 (e.g., a blower). However, unlike those apparatus previously set forth, the motor speed of the flow generator is controlled by a central processing unit (CPU) 136. The apparatus also includes a suitable patient condition sensor means such as a pressure transducer 138 situated within or near the breathing circuit, i.e., the breathing mask 22, conduit means 20 or gas flow generator 14. In its most general form, the pressure transducer 138 is a differential pressure sensor capable of detecting selected pressure differentials in the patient's breathing circuit associated with pressure or pressures of selected magnitude and/or frequency. A preferred, although not limitative, embodiment of the pressure transducer 138 is an audio transducer or microphone. When, for example, snoring sounds occur the pressure transducer detects the sounds and feeds corresponding electrical impulses to the CPU 136 which, in turn, generates a flow generator motor control signal. Such signal increases the speed of the flow generator motor, thereby increasing output pressure supplied to the patient through the pressure controller 26 and conduit means 20.

As snoring is caused by vibration of the soft palate, it is therefore indicative of an unstable airway and is a warning signal of the imminence of upper airway occlusion in patients that suffer obstructive sleep apnea. Snoring is itself undesirable not only as it is a disturbance to others but it is strongly believed to be connected with hypertension. If the resultant increase in system output pressure is sufficient to completely stabilize the airway, snoring will cease. If a further snoring sound is detected, the pressure is again incrementally increased. This process is repeated until the upper airway is stabilized and snoring ceases. Hence, the occurrence of obstructive apnea can be eliminated by application of minimum appropriate pressure at the time of use.

In apparatus such as that disclosed in U.S. Pat. No. 5,199,424, the feedback circuit includes means to gradually decrease the output pressure if an extended period of snore-free breathing occurs in order to ensure that the pressure is maintained at a level as low as practicable to prevent the onset of apnea. The feedback circuit of the present invention as shown in FIGS. 10 through 15 preferably includes similar means. This effect can be achieved, for example, by the CPU 136 which, in the absence of an electronic signal from the pressure transducer 138 indicative of snoring, continuously and gradually reduces the flow generator speed and output pressure over a period of time. If, however, a snore is detected by the first pressure transducer, the CPU will again act to incrementally increase the output of the flow generator.

In use, a patient may connect himself to the apparatus 210 and go to sleep. The output pressure is initially at a minimum operating value of, for example, approximately 3 cm H$_2$O gauge pressure so as not to cause the previously mentioned operational problems of higher initial pressures. Not until some time after going to sleep, the patient's body relaxes, will the airway start to become unstable and the patient begin to snore. The pressure transducer 138 will then respond to a snore, or snore pattern, and via the CPU 136 increase the flow generator motor speed such that output pressure increases, for instance, by 1 cm H₂O for each snore detected. The pressure can be increased relatively rapidly, if the patient's condition so requires, to a working pressure of the order of 8–20 cm, which is a typical requirement. An upper pressure limiting device, to be described later herein, can be incorporated for safety. Additionally, for ease of monitoring the variation over time a parameter such as pressure output can be recorded in some convenient retrievable form and medium (a preferred embodiment of which is also later described) for periodic study by the physician.

If for example in the early stages of sleep some lesser output pressure will suffice, the apparatus of the present invention will not increase the pressure until needed, that is, unless the airway becomes unstable and snoring commences no increase in airway pressure is made.

By continuously decreasing the output pressure at a rate of, for example, 1 cm H₂O each 15 minutes in the absence of snoring, the pressure is never substantially greater than that required to prevent apnea. However, such elevated pressure may be somewhat uncomfortable to the patient should he suddenly awaken and immediately wish to resume therapy at a minimum pressure to facilitate has transition back to a sleeping state. A preferred approach for alleviating this particular phenomenon is addressed later herein in connection with the discussion of FIG. 12.

Like other feedback type positive airway pressure ventilation apparatus known to those skilled in the art, the feedback circuit of FIGS. 10–15 provides a device which adjusts apparatus output pressure according to variations in a patient's breathing requirements throughout an entire sleep period. Further, it will be understood that the present invention as represented in FIGS. 10 through 15 will likewise accommodate variable output pressure requirements owing to general improvements or deteriorations in a patient's general physical condition as may occur over an extended period of time.

Still referring to FIG. 10, it is revealed that the embodiment of the apparatus 210 represented therein, apart from its patient-responsive variable pressure output capability, may also be provided with ramp control circuitry means 104, 104' of the types possessing the characteristics described in detail in connection with the discussion of FIGS. 7A and 7B. That is to say, apparatus 210 may also include ramp control circuitry means connected to the pressure controller 26 for effecting (1) a first ramp cycle wherein gas flow from the pressure controller is initially output at a first pressure and raises with time to a second pressure, and (2) at least one additional selectively activable ramp cycle. Pursuant thereto, the ramp control circuitry means 104, 104' may include, inter alia, means for adjusting the magnitudes of the first and second ramp pressures, as well as means for adjusting the durations and/or pressure patterns of the first and any additional ramp cycles. And, like the apparatus of FIGS. 5A the activation of the apparatus 210 as well as its ramp cycles may be achieved through suitable manipulation of appropriate manually manipulable actuators, such as buttons, switches, or the like, provided on a remote control 106.

Figure 11:
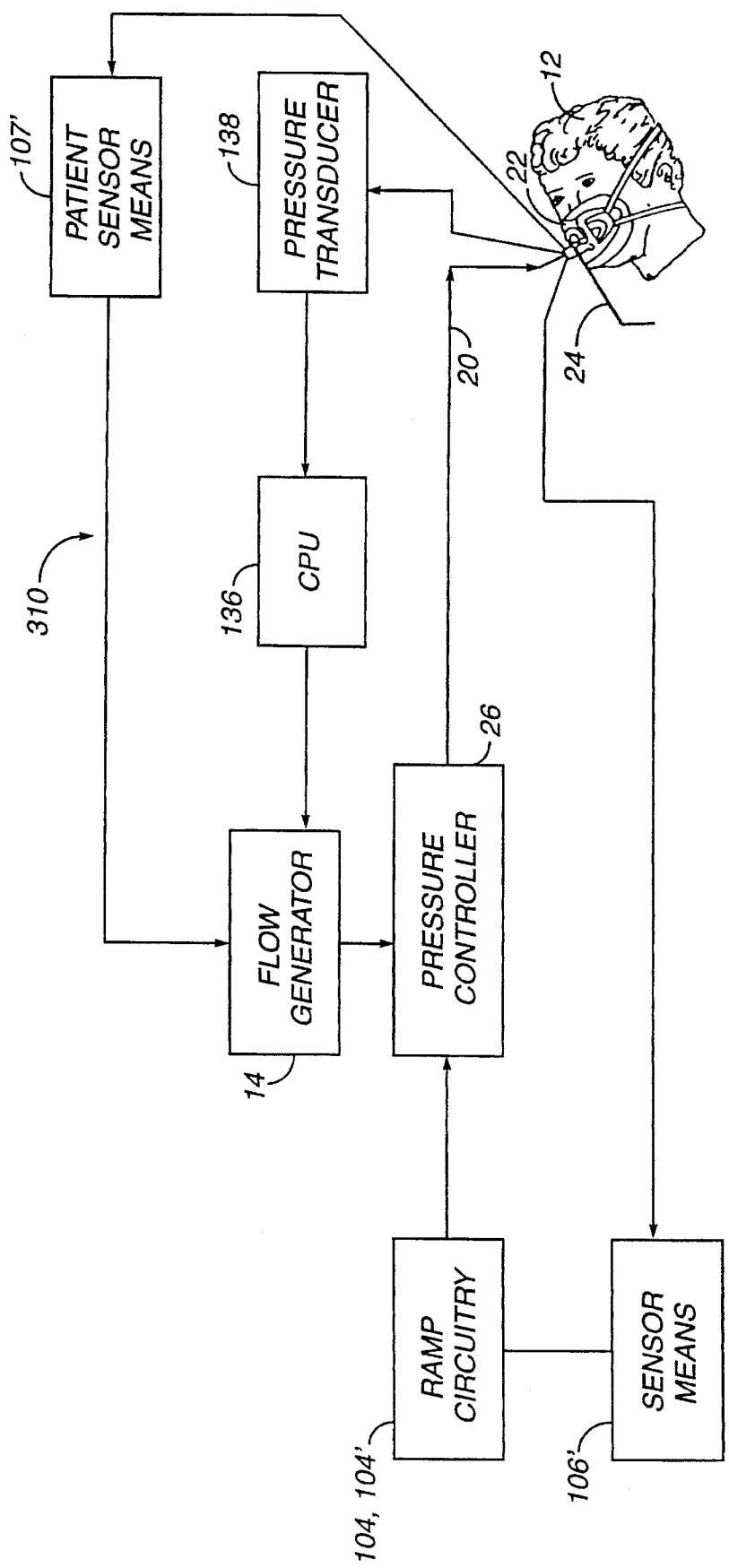
FIG. 11 is a functional block diagram of a further embodiment of an apparatus according to the instant invention.

FIG. 11 represents an apparatus, herein designated by reference numeral 310, which desirably incorporates the features of a feedback type positive airway pressure ventilation apparatus with a patient sensor means 107' and sensor means 106' of the types discussed in regard to the apparatus 10' of FIG. 5A. Thus, the apparatus 310 preferably includes a patient sensor means 107' such as a pressure, flow, thermal, audio, optic, electrical current, voltage, force or displacement transducer. The patient sensor means may be situated within or proximate the patient's breathing circuit which comprises gas conduit 20, gas flow generator 14 and a suitable respiratory interface such as respiratory mask 22 and is operable to detect the pressure (and/or absence) of the patient so as to automatically control activation and deactivation of the apparatus. Accordingly, pursuant to a first mode of operation when the mask is appropriately positioned over the patient's face, the sensor means 107' will detect the patient's presence and generate a signal that is transmitted to the flow generator 14 to activate the apparatus. In a second operational mode, the patient sensor means may function exclusively to deactivate the apparatus. Thus, upon removal of the mask, the sensor would fail to detect any conditions indicative of the patient's presence and generate and transmit a signal to deactivate the apparatus. And, as with the patient sensor means of FIG. 5A, a third modality combines these functions. That is to say, the patient sensor means 107' may be operable to detect the presence and absence of the patient and generate a signal to activate the apparatus upon detection of a condition indicative of the patient's presence, as well as an apparatus deactivation signal upon failure of detecting such a signal, i.e., the patient's absence.

Likewise, the sensor means 106' may function in the manner of its counterpart, sensor means 106' of FIG. 5A, i.e., as a substitute for a manually manipulable ramp activation button, switch, or the like, provided on a remote control device such as remote control 106 of FIGS. 5 and 10. Thus, the sensor means 106' may comprise any suitable sensor means responsive to predetermined signals consciously produced by the patient. Again, pursuant to a presently preferred construction, the sensor means 106' comprise a pressure transducer responsive to a pressure or pressures of selected magnitude and/or frequency. For instance, sensor means 106' may be a microphone located within the patient's breathing circuit or gas flow system (i.e., in or near the patient's respiratory interface, associated gas flow conduit or gas flow generator) and capable of detecting sound waves of a limited frequency range substantially spanning that associated with human speech. Constructed and arranged as such, the transducer would be nonresponsive to common ambient sounds produced by the patient (e.g., coughing or sneezing), machinery noise, music or animal sounds. Moreover, by being isolated through its enclosure within the gas flow system, the transducer 106' would detect only the patient's speech to the exclusion of others in the vicinity or speech emanating from television or radio sources. Upon detection of the patient's speech such as, for example, when the patient awakens and then speaks to initiate a new ramp cycle to facilitate transition to a sleeping state, the transducer generates and transmits an activation signal to the ramp control circuitry means 104,104' to initiate the desired ramp cycle. The ramp activation sensor means 106' may alternatively be operable to begin a ramp cycle in response to detection of a predetermined pattern of inhalations and/or exhalations or other conscious actions by the patient.

Figure 12:
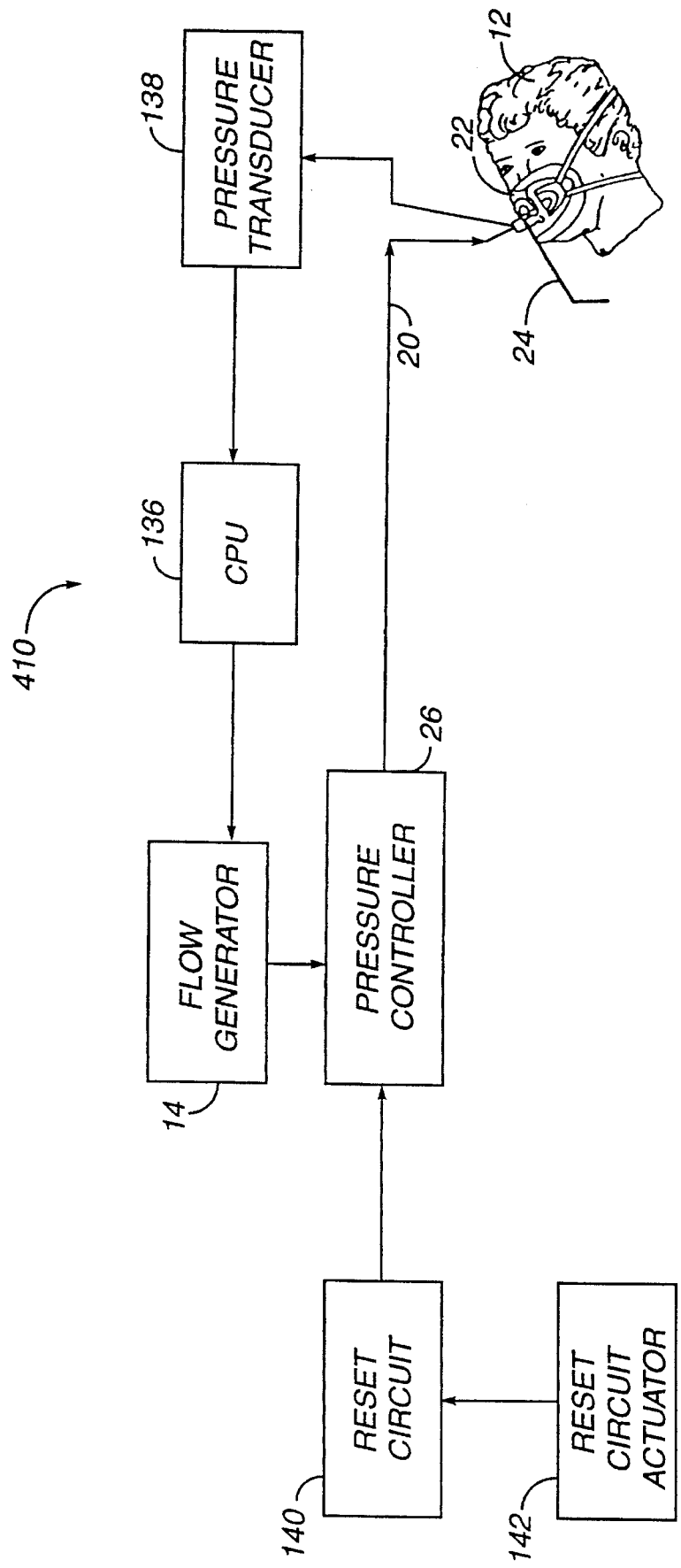
FIG. 12 is a functional block diagram of a further embodiment of an apparatus according to the instant invention.

FIG. 12 reveals an apparatus 410 constructed according to a further embodiment of the present invention. Like apparatus 210 and 310, apparatus 410 is of the feedback type whose operation has been generally discussed above in connection with FIG. 10. Apparatus 410 additionally includes reset circuitry means or "reset circuit" 140. The reset circuit 140 permits the patient (if suddenly awakened, for instance) to instantaneously reset the system output pressure to a predetermined reduced pressure whereupon the treatment may then proceed as it did prior to reset. An advantage attendant to the ramp control circuitry means 104, 104' and the reset circuit 140 is that they both afford the patient the opportunity to immediately respire against a reduced pressure once awakened, thereby enhancing comfort and transition back to a sleeping state. The following example will assist the reader in conceptualizing the value of these features.

Suppose that the patient is experiencing feedback type positive airway pressure therapy and awakens for whatever reason. It will be appreciated that under such circumstances the patient will, upon awakening, likely be experiencing a somewhat elevated airway pressure, even if the ventilation apparatus were functioning in the gradually decreasing output pressure mode associated with an extended period of snore-free breathing. To achieve a comfortable output pressure conducive to the patient's falling back to sleep, the patient would either have to wait until the output pressure reaches a comfortable level (which may take up to an hour or longer). Alternatively, the patient would be required to deactivate the entire apparatus, perform any system checks, e.g., leakage tests, which may be required to assure proper functioning of the apparatus and wait until the apparatus returns to its normal operational mode.

In accordance with the present system, however, the patient merely operates a reset circuit actuator 142 to effect activation of the reset circuit 140 and thereby instantaneously reset the apparatus 410 to resume therapy. Consistent with other embodiments of the invention thus far described, the reset circuit actuator 142 may assume the form for a manually manipulable button, switch, or the like, provided directly on the apparatus housing or on a remote control such as remote control 106 of FIGS. 5 and 10. If constructed in such a fashion, the reset circuit actuator desirably will have a substantially different physical configuration than the apparatus activation and ramp activation actuators whereby it can be readily identified by the patient by either sight or touch. As an alternative construction, the reset circuit actuator may be a sensor means similar to sensor means 106' of FIGS. 5A and 11.

Unlike the ramp control circuitry means 104, 104' however, the reset circuit 140 of FIG. 12 permits the patient, when such is desired or necessary, to more rapidly receive the full benefits of the positive airway pressure therapy since therapy resumes instantaneously upon reset. As will be appreciated, the reset circuit 140 rather than the ramp control circuitry means 104,104 ' is more likely to be activated by a patient who generally experiences little difficulty in falling back to sleep once awakened.

Figure 13:
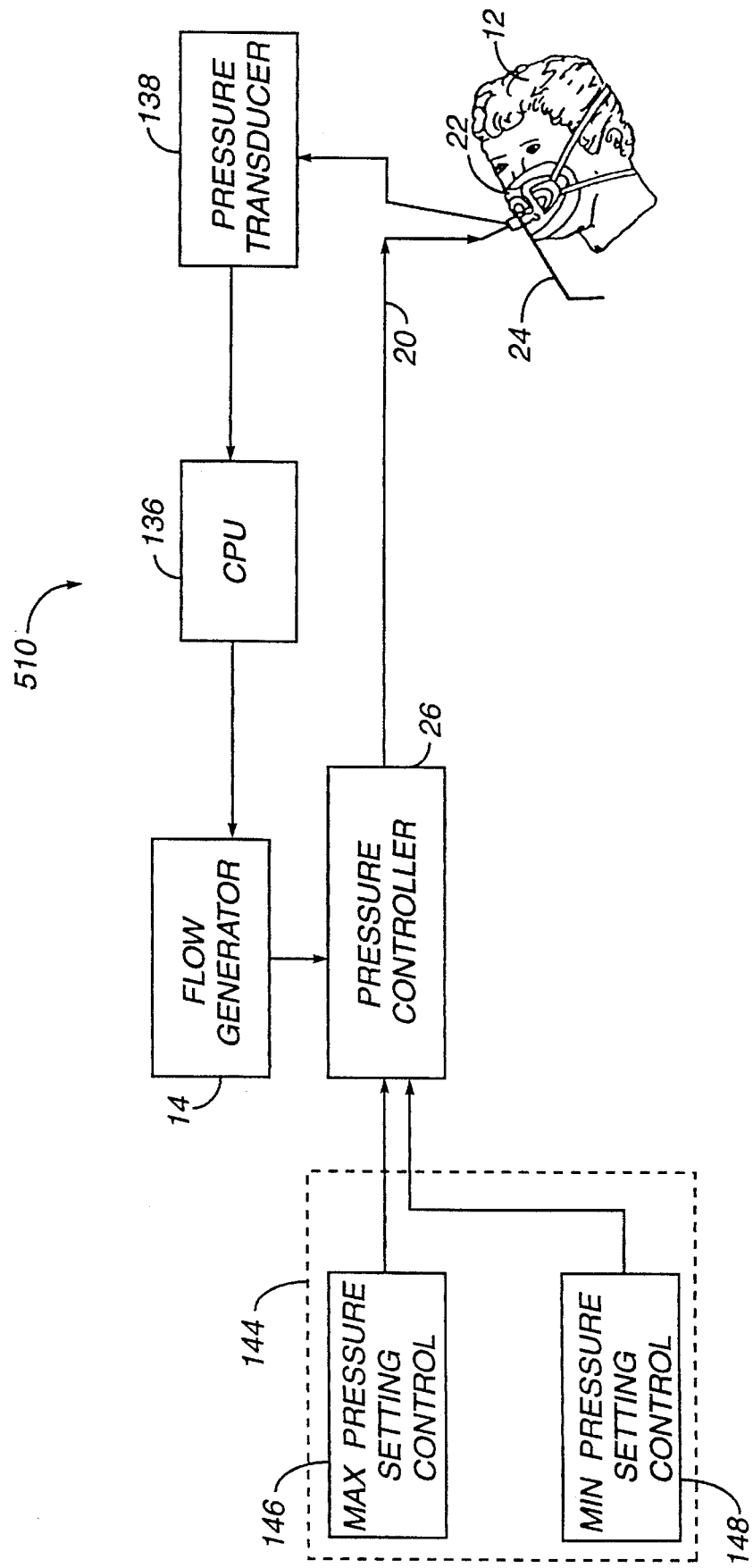
FIG. 13 is a functional block diagram of a further embodiment of an apparatus according to the instant invention.

A further embodiment of the present invention is shown in FIG. 13. Again, there is provided a feedback type positive airway pressure ventilation apparatus, reference numeral 510, in this instance also including a safety circuit 144 comprising an adjustable maximum pressure setting control 146 and an adjustable minimum pressure setting control 148.

The safety circuit 144 allows the manufacturer, the patient or his overseeing health care professional to selectively establish minimum and maximum system output pressures below and above which the system will not dispense pressurized gas. The minimum pressure will, of course, be at least zero and, preferably, a threshold pressure sufficient to maintain pharyngeal patency during expiration. The maximum pressure, on the other hand, will be some pressure somewhat less than that which would result in over-inflation and perhaps rupture of the patient's lungs. The safety circuit functions differently than the pressure controls 116 and 122 of the ramp control circuitry means 104, 104'. That is, instead of establishing lower and upper prescription pressures to be applied during normal usage of the apparatus, it sets absolute minimum and maximum fail-safe output pressure limits which are not to be exceeded, and therefore potentially cause physical harm to the patient in the event the other system components, e.g., the feedback circuit, or the prescription pressure controls of the ramp control circuitry means, malfunction.

Figure 14:
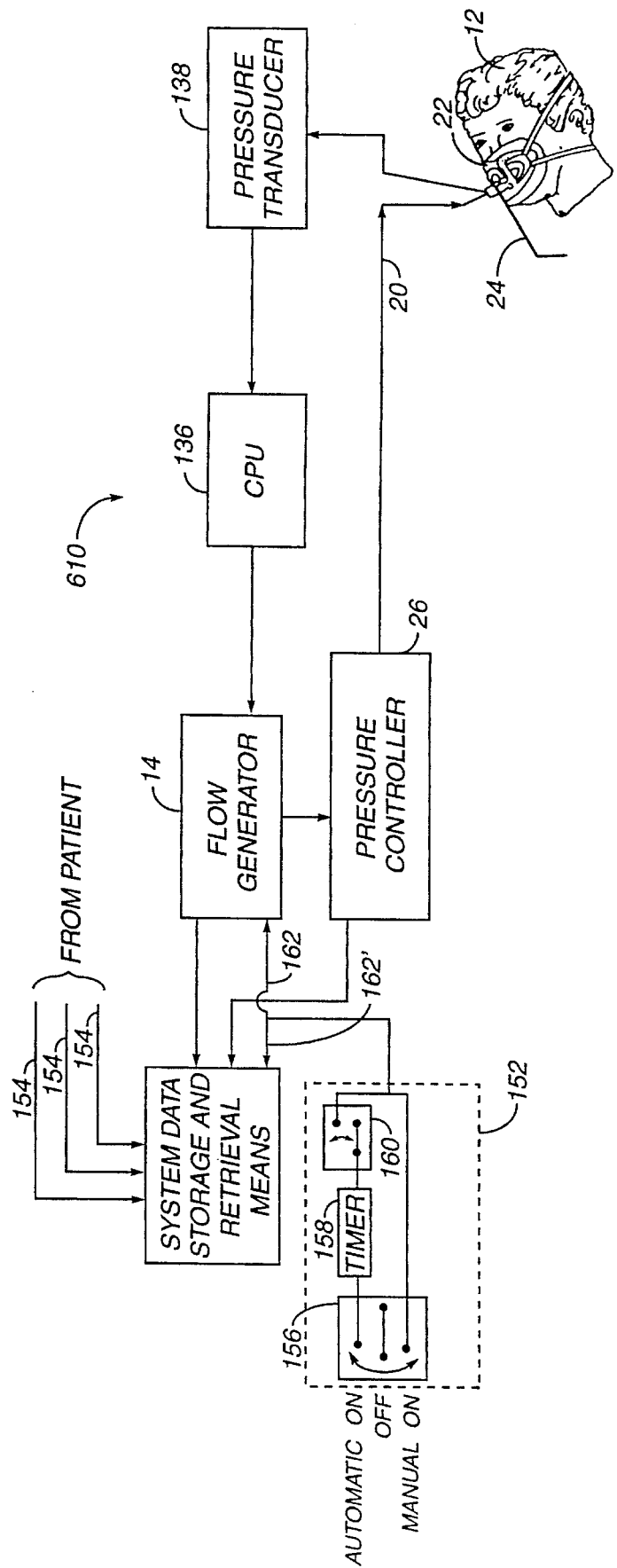
FIG. 14 is a functional block diagram of a further embodiment of an apparatus according to the instant invention.

The embodiment according to FIG. 14, which is generally identified by reference numeral 610, includes the aforesaid pressure feedback circuit as well as system data storage and retrieval means 150 and a therapy delay circuit 152. Apparatus 610 represents an embodiment of the instant invention which finds primary application in the "clinical" environment, i.e., in a sleep study of the patient performed in a hospital, clinic or laboratory.

System data storage and retrieval means 150 may within the scope of the present invention comprise any suitable computer memory into which information can be read and from which information can be written. Representative, although not limitative, embodiments of the system data storage and retrieval means may therefore include a random access memory (RAM), magnetic tapes or magnetic disks which may be incorporated into a stand-alone personal computer, mainframe computer, or the like (not illustrated). In cooperation with the system data storage and retrieval means 150, the therapy delay circuit 152 permits a patient's sleep disorder to be diagnosed and treated during a single sleep study. Stated differently, in a marked departure from other clinical diagnosis/treatment systems presently known to the inventors to be employed in the subject art, the apparatus 610 of FIG. 14 can under many, if not all, circumstances enable diagnosis and treatment of the patient's respiratory-related sleep disorder in a single night at the sleep study facility.

In this connection, the typical practice has been for the patient to undergo two sleep studies at an appropriate observation facility such as a hospital, clinic or laboratory. The first night is spent observing the patient in sleep and recording data associated with selected physiological parameters such as oxygen saturation, chest wall and abdominal movement, air flow, expired $CO_2$, ECG, EEG, EMG and eye movement. This information can then be interpreted to diagnose the nature of the sleeping disorder and confirm the presence or absence of apnea and, where present, the frequency of apneic episodes and extent and duration of associated oxygen desaturation. Apneas can be identified as obstructive, central or mixed.

The second night is spent with the patient undergoing positive airway pressure therapy. When apnea is observed the pressure setting is increased as required to determine the maximum pressure necessary to prevent apnea. For a given patient in a given physical condition there normally will be found different minimum pressures for various stages of sleep in order to prevent occlusions.

In order to condense the present practice of a two night sleep study into a single night, the therapy delay circuit 152 of the instant invention is operable to suppress the application of positive airway pressure therapy for any desired period of time, e.g., several hours, while the system data storage and retrieval means compile data from one or more data input lines 154 which communicate data associated with the patient's physiological parameters necessary for proper diagnosis of the patient's particular sleep disorder. Once sufficient data is recorded in the system data storage and retrieval means 150, system control adjustments based upon the data including, but not limited to, absolute maximum and minimum system output pressures (FIG. 13), and ramp prescription pressures, durations and patterns (FIGS. 10 and 11), may be inputted as appropriate and the therapy delay circuit 152 may be switched from its therapy suppression mode to a therapy application mode, whereby treatment specifically responsive to conditions observed during diagnosis may be effectively implemented in a single night in the sleep study facility. The terms "suppress" and its conjugates in the present context will be understood to mean limiting pressure output of the apparatus from a value of at least zero and up to a predetermined value which is usually below a normal therapeutic output pressure.

An exemplary construction of the therapy delay circuit 152 is illustrated in FIG. 14. The circuit 152 may include a three-position switch 156 (shown in its open or "OFF" position) which preferably is adapted for use in an "automatic" therapy delay or suppression mode of the circuit. Switch 156 is electrically connected to an adjustable timer 158. Timer 158 may be infinitely adjustable for any time period from about 0 to 8 hours. The timer is, in turn, connected to and automatically controls a two-position switch 160 (also shown in its open or "OFF" position).

When it is desired to operate the therapy delay circuit in the automatic mode, the clinician or other health care professional monitoring the patient's sleep study adjusts the timer 158 to a desired therapy delay period, e.g., 3 to 4 hours, and positions the switch 156 to the "AUTOMATIC ON" position. During the established therapy delay period the patient falls asleep, the feedback circuit is suppressed and the system data storage and retrieval means 150 compiles physiological data gathered from the patient and transmitted by data input lines 154. At the expiration of the therapy delay period, any system pressure and other parameters may be appropriately adjusted by the clinician and the timer automatically closes switch 160, i.e., places it into its "ON" position, to send therapy activation signal 162 to the flow generator 14 to cause the feedback circuit of apparatus 610 to provide the patient with ventilation therapy particularly suited to his sleep disorder requirements.

Simultaneously, a signal 162' is transmitted to the system data storage and retrieval means 150. The signal 162' serves as a control signal which may be selected by the apparatus operator to either deactivate means 150 during therapy or to cause means 150 to collect data from the patient data input lines 154, flow generator 14, pressure controller 26 and/or other selected sources during therapy. Upon deactivation of the apparatus following completion of a therapy session both switches 156 and 160 automatically return to their open or "OFF" positions.

Switch 156 may also be switched into a "manual" mode whereby the timer 158 and switch 160 are bypassed. Thus, when the switch 156 is placed into the "MANUAL ON" position, such as when the apparatus operator is satisfied that sufficient diagnostic data has been compiled, signals 162 and 162' are respectively transmitted to the flow generator 14 and system data storage and retrieval means 150.

Although, as noted above, the system data storage and retrieval means 150 and delay therapy circuit 152 find their primary usage in the sleep study facility, such components may also be incorporated into the patient's home ventilation apparatus as well. Under such circumstances, the patient can, with proper instruction, personally monitor the progress or deterioration of his therapy over a period of time and adjust the therapy parameters as necessary. In either case, provision of the system data storage and retrieval means and therapy delay circuit enable the user to spend less time in the sleep study facility or under direct supervision of a professional health care worker, hence reducing therapy cost and inconvenience.

Figure 15:
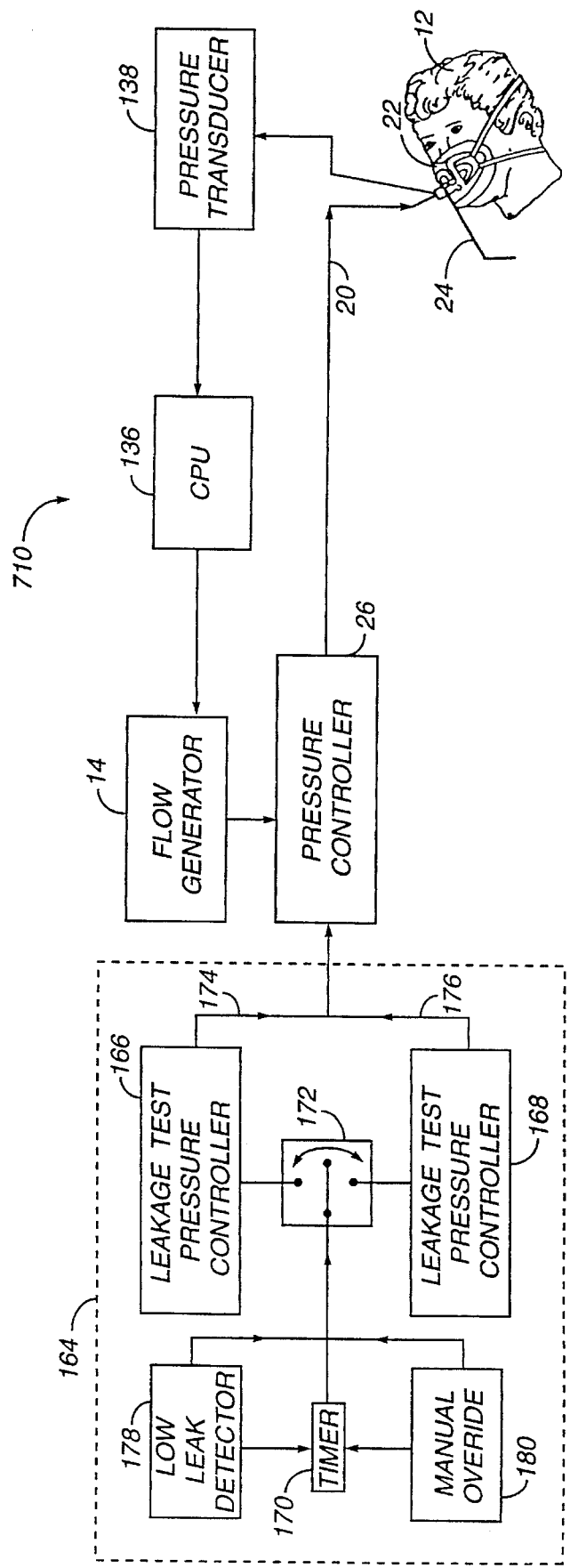
FIG. 15 is a functional block diagram of a further embodiment of an apparatus according to the instant invention.

FIG. 15 represents a further embodiment of the present invention. According to this embodiment, the positive airway pressure apparatus (reference numeral 710) comprises the above-described feedback circuit and a minimum system leakage assurance circuit 164, the function of which is to assure that the system discharges a minimum leakage flow during therapy, i.e., when the patient is asleep or attempting to fall asleep. The minimum system leakage assurance circuit 164 desirably comprises an adjustable leakage test pressure control 166, an adjustable pre-therapy control 168, an adjustable timer 170 and a three-position switch 172. The switch 172 is responsive to the timer 170 and triggers the leakage test pressure control 166 to transmit a signal 174 causing the apparatus 710 to output a preset leakage test pressure. The switch is also operable to trigger the pre-therapy pressure control 168 to transmit a signal 176 causing the apparatus to output a preset pre-therapy pressure. The preset leakage test pressure is a relatively high pressure and may, for instance, be the peak pressure output by the apparatus during the previous night or some other desired pressure. Similarly, the pre-therapy pressure is a relatively low pressure and may be the minimum pressure output by the apparatus during the previous night or some other pressure.

Using the timer 170, after the apparatus is activated the system will output the leakage test pressure to temporarily overpressurize the gas flow circuit for some preselected period of time. This time period (e.g. several seconds) would normally be sufficient for the patient to properly position and seal the respiratory interface, e.g., mask 22, on his face and adjust any gas conduit connections such that system leakage flow is brought to a minimum. After expiration of the prescribed period of time, the timer triggers the switch 172 to activate the therapy pressure control 168 to transmit signal 176, thereby causing the system to output the selected pre-therapy pressure for a specified duration also established by the timer. After expiration of the designated time for pre-therapy pressure application, the timer then urges the switch to assume a neutral or "OFF" position whereby the apparatus outputs its designated positive airway pressure therapy.

An advantage of such an arrangement is that by temporarily overpressurizing the gas flow circuit prior to treatment, unwanted system leaks can be discovered and sealed before the patient falls asleep. Hence, leakage flow (or average system flow) and its associated pressure can be minimized while the patient sleeps, thereby enhancing patient comfort. In lieu of or addition to the timer 170, the minimum system leakage assurance circuit 164 may also include a low leak detector 178. The low leak detector detects whether the system, under the application the leak test pressure (which may be programmed to be output automatically upon apparatus activation), outputs a leakage flow less than a predetermined minimum leakage flow. If a sufficiently low leakage flow is detected, the low leak detector automatically overrides the timer (if present) and triggers the pre-therapy pressure control 168 to cause the system to output the specified pre-therapy pressure for a preset time and then output the appropriate therapy pressure.

Similarly, in addition to or in lieu of the timer 170 and/or the low leak detector 178, the minimum system leakage assurance circuitry may include a manual override 180, e.g., a button, switch or patient-responsive transducer, which responds to patient initiated commands to override the timer and/or low leak detector (if present).

For clarity of illustration and description, the various apparatus control circuits of FIGS. 10 through 15 are depicted as being individually associated with the positive airway pressure feedback circuits of those figures. However, under many, if not all, circumstances there will in fact be more than one of the ramp control circuitry means 104, 104', reset circuit 140, safety circuit 144, therapy delay circuit 152 (and system data storage and retrieval means 150), and minimum system leakage assurance circuit 164 present in the ventilation apparatus. Indeed, it is contemplated that these circuits may coexist in any combination with one another, as well as with other ventilation control components known to those skilled in the art.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. Apparatus for delivering pressurized gas to the airway of a patent, said apparatus comprising:

gas flow generator means for providing a flow of said gas;

conduit means for delivery of said gas flow to the airway of said patient;

pressure controller means cooperable with said gas flow generator means to provide for flow of said gas within said conduit means and within the airway of said patient at at least one pressure level; and reset circuit means for permitting said patient to substantially instantaneously reset said pressure controller means to provide said flow of gas at a predetermined reduced pressure after which said pressure controller means resumes provision of said flow of gas in a manner substantially similar to that provided prior to said reset.

2. The apparatus of claim 1 wherein said apparatus is a mono-level positive airway pressure apparatus.

3. The apparatus of claim 1 wherein said apparatus is a bi-level positive airway pressure apparatus.

4. The apparatus of claim 1 wherein said apparatus is a variable level positive airway pressure apparatus.

5. The apparatus of claim 1 further comprising feedback circuit means for controlling said gas flow generator means responsive to detection of a condition associated with said patient.

6. The apparatus of claim 1 wherein said apparatus further comprises means for actuating said reset circuit to effect said reset.

7. The apparatus of claim 1 further comprising system data storage and retrieval means for compiling data associated with physiological parameters of said patient.

* * * * *